(12) United States Patent
Sobe

(10) Patent No.: US 7,881,769 B2
(45) Date of Patent: Feb. 1, 2011

(54) METHOD AND SYSTEM FOR MOUNTING AN MPS SENSOR ON A CATHETER

(75) Inventor: Lior Sobe, Ra'anana (IL)

(73) Assignee: MediGuide Ltd., Haifa (IL)

(*) Notice: Subject to any disclaimer, the term of this patent is extended or adjusted under 35 U.S.C. 154(b) by 667 days.

(21) Appl. No.: 10/408,156

(22) Filed: Apr. 7, 2003

(65) Prior Publication Data

US 2004/0097804 A1     May 20, 2004

Related U.S. Application Data

(63) Continuation of application No. 10/298,358, filed on Nov. 18, 2002, now abandoned.

(51) Int. Cl.
*A61B 5/05* (2006.01)
(52) U.S. Cl. ...................................... 600/424
(58) Field of Classification Search ............... 600/424, 600/427, 429, 117, 409, 407, 114, 118, 300, 600/317, 479, 481–488, 460–463, 410, 100, 600/160; 128/196; 604/49–53, 508–522
See application file for complete search history.

(56) References Cited

U.S. PATENT DOCUMENTS

| 5,489,271 | A |   | 2/1996 | Andersen ................... 604/102 |
| 5,588,432 | A | * | 12/1996 | Crowley ..................... 600/439 |
| 5,830,222 | A |   | 11/1998 | Makower .................... 606/159 |
| 5,840,024 | A | * | 11/1998 | Taniguchi et al. ........... 600/424 |
| 5,873,835 | A |   | 2/1999 | Hastings et al. |
| 5,897,529 | A |   | 4/1999 | Ponzi ........................ 604/95 |
| 5,916,241 | A | * | 6/1999 | Rudie et al. ................ 607/101 |
| 5,928,248 | A |   | 7/1999 | Acker ........................ 606/108 |
| 6,035,856 | A |   | 3/2000 | LaFontaine et al. ......... 128/898 |
| 6,179,811 | B1 |  | 1/2001 | Fugoso et al. ............ 604/96.01 |
| 6,203,493 | B1 | * | 3/2001 | Ben-Haim .................. 600/117 |
| 6,231,516 | B1 | * | 5/2001 | Keilman et al. ............. 600/485 |
| 6,233,476 | B1 |  | 5/2001 | Strommer et al. ........... 600/424 |
| 6,251,107 | B1 |  | 6/2001 | Schaer |
| 6,253,770 | B1 | * | 7/2001 | Acker et al. ................ 128/899 |
| 6,298,259 | B1 | * | 10/2001 | Kucharczyk et al. ........ 600/411 |
| 6,427,079 | B1 | * | 7/2002 | Schneider et al. ........... 600/424 |
| 6,509,521 | B1 | * | 1/2003 | Geitz ......................... 174/28 |
| 6,618,612 | B1 | * | 9/2003 | Acker et al. ................ 600/424 |
| 6,689,049 | B1 | * | 2/2004 | Miyagi et al. ............... 600/117 |

(Continued)

FOREIGN PATENT DOCUMENTS

WO     WO96/05768     2/1996

OTHER PUBLICATIONS

"PTCA with Stent" http://www.bostonscientific.com/common_templates/articleDisplayTemplate.jhtml?task=tskProcedureOverview.jhtml&sectionId=4&re1Id=2,63,64&procedureId=94.

(Continued)

*Primary Examiner*—Brian Casler
*Assistant Examiner*—Joel M Lamprecht
(74) *Attorney, Agent, or Firm*—Dykema Gossett PLLC

(57) ABSTRACT

Catheter for performing a medical operation on an organic lumen, the catheter including an elongated member, a medical operational element located at a distal end of the elongated member, an electromagnetic field detector located at the distal end, and a wiring for coupling the electromagnetic field detector with a medical positioning system, wherein the medical positioning system determines the position and orientation of the distal end.

21 Claims, 17 Drawing Sheets

U.S. PATENT DOCUMENTS

| | | |
|---|---|---|
| 6,690,963 B2 * | 2/2004 | Ben-Haim et al. .......... 600/424 |
| 2002/0016589 A1 * | 2/2002 | Swartz et al. ................. 606/41 |
| 2002/0099364 A1 * | 7/2002 | Lalonde ....................... 606/21 |
| 2002/0128537 A1 | 9/2002 | Watanabe et al. |
| 2002/0143371 A1 | 10/2002 | Balczewski et al. |

OTHER PUBLICATIONS

"The Interventional Cardiac Catheterization Handbook" Morton J. Kern, $3^{rd}$ Edition, Mosby-Year Book Inc., 1999 pp. 17-43, 72-74, 80-101, 224-250 and 393-436.

International Search Report; PCT Application No. PCT/IL03/00940 dated Feb. 28, 2006.

* cited by examiner

METHOD AND SYSTEM FOR MOUNTING AN MPS SENSOR ON A CATHETER

This is a continuation of application Ser. No. 10/298,358, filed Nov. 18, 2002 now abandoned. The prior applications is hereby incorporated herein by reference, it its entirety.

FIELD OF THE DISCLOSED TECHNIQUE

The disclosed technique relates to medical devices in general, and to methods and systems for determining the position and orientation of a catheter, in particular.

BACKGROUND OF THE DISCLOSED TECHNIQUE

Medical operations on human or animal lumens, such as the vascular system, ureter, urethra, brain vessels, coronary vessels, lumens of the liver, kidney, lung, digestive system, and the like, can be performed by employing a medical catheter. Such medical operations include dilating a lumen by a balloon or a stent, implanting a stent, delivering a pharmaceutical substance to the lumen, performing coronary bypass, removing plaque from the intima of a blood vessel, implanting a graft, and the like. Such a medical catheter includes a lumen intervention element, such as a balloon, stent, balloon expanding stent, substance delivery element, tissue severing element, and the like, at the distal end thereof.

In some cases, the medical catheter also includes a radiopaque material at the distal end, which serves as a marker for the location of the distal end. In order to perform the medical operation, usually a guiding catheter is initially inserted in the lumen. Sometimes an auxiliary, large-diameter guidewire is inserted prior to the guiding catheter for aiding it to enable manipulation of the guiding catheter. Next, the large-diameter guidewire is pulled out, another guidewire, with of smaller diameter, is inserted in the guiding catheter and the small-diameter guidewire is advanced to the desired location within the lumen, by manipulating the tip of the small-diameter guidewire from outside the body of the patient. The proximal end of the small-diameter guidewire is inserted into the distal end of the medical catheter and the medical catheter is advanced to the desired location, by passing the medical catheter over the guidewire inside the guiding catheter. The physician determines the position of the distal end of the medical catheter, by viewing an image of the marker in an imaging device, such as fluoroscope, X-ray table, and the like. When the physician assures that the lumen intervention element is located at the desired location, the physician performs the medical task on the lumen.

U.S. Pat. No. 6,233,476 issued to Strommer et al., assigned to the present assignee, and entitled "Medical Positioning System", is directed to a medical positioning system (MPS) for determining the position and orientation of a medical device within a living tissue. The MPS includes a 3D electromagnetic field (EMF) generator, a main sensor, an auxiliary sensor, a sensor interface, a position and orientation processor, a superimposing processor, an image interface, a 3D image database and a display unit.

The position and orientation processor is connected to the 3D EMF generator, the sensor interface and to the superimposing processor. The auxiliary sensor and the main sensor are connected to the sensor interface. The image interface is connected to the superimposing processor and to the 3D image database. The display unit is connected to the superimposing processor. The main sensor is located at the tip of the medical device. The auxiliary sensor is located in the vicinity of the inspected tissue of the patient.

The 3D image database includes a plurality of predetected images of the inspected tissue of the patient. The auxiliary sensor compensates for the movement of the patient. The 3D EMF generator includes a plurality of electromagnetic coils that produce electromagnetic fields in different directions and in different magnitudes. Each of the main sensor and the auxiliary sensor includes three electromagnetic coils. Each of the electromagnetic coils of the main sensor and the auxiliary sensor detects an electromagnetic field in a different direction. Each of the main sensor and the auxiliary sensor produces a signal in response to the electromagnetic field generated by the 3D EMF generator, corresponding to the position and orientation of the main sensor and the auxiliary sensor, respectively.

The position and orientation processor receives the signal from the main sensor through the sensor interface and the position and orientation processor determines the position and orientation of the main sensor according to this signal. The superimposing processor retrieves a predetected image of the inspected tissue from the 3D image database, through the image interface. The superimposing processor superimposes a representation of the tip of the medical device on the retrieved image and produces a video signal. The representation of the tip of the medical device corresponds to the position and orientation of the tip of the medical device relative to the inspected tissue. The display unit produces a video image according to the video signal. U.S. Pat. No. 5,646,525 issued to Gilboa and entitled "Three Dimensional Tracking System Employing a Rotating Field", provides a description of three dimensional tracking system employed by the MPS for determining position and orientation.

U.S. Pat. No. 6,179,811 issued to Fugoso, et al., and entitled "Imbedded Marker and Flexible Guide Wire Shaft", is directed to a balloon catheter which includes a marker band imbedded into a guidewire shaft of the balloon catheter. The balloon catheter includes a balloon, a shaft, a manifold, a guidewire shaft and a plurality of marker bands. The guidewire shaft is located within the shaft. The proximal end of the balloon is affixed to a distal end of the shaft and the distal end of the balloon is bonded to a distal end of the guidewire shaft. The manifold is located at a proximal end of the shaft. The marker bands are imbedded into the guidewire shaft at a region of the guidewire shaft below the balloon. The marker bands can be viewed by fluoroscope equipment.

U.S. Pat. No. 5,928,248 issued to Acker and entitled "Guided Deployment of Stents.", is directed to an apparatus for applying a stent in a tubular structure of a patient. The apparatus includes a catheter, a hub, a pressure control device, a balloon, a stent, a probe field transducer, a plurality of external field transducers, a field transmitting and receiving device, a computer, an input device and a cathode ray tube. The catheter includes a bore. The hub is affixed to a proximal end of the catheter. The balloon is mounted on a distal end of the catheter. The pressure control device is connected to the balloon through the hub and the bore. The stent is made of a shape memory alloy and is located on the balloon.

The probe field transducer is located within the catheter, at a distal end thereof. The external field transducers are located outside of the patient (e.g., connected to the patient-supporting bed). The field transmitting and receiving device is connected to the external field transducers, the probe field transducer and to the computer. The computer is connected to the cathode ray tube and to the input device.

A user calibrates the field transmitting and receiving device in an external field of reference, by employing the external field transducers. The field transmitting and receiving device together with the computer, determine the position and orientation of the probe field transducer in the external field of reference. The user views the position and orientation of a representation of the stent which is located within a tubular structure of the patient, on the cathode ray tube. When the user determines that the distal end is located at the desired location within the tubular structure, the user expands the stent by operating the pressure control device and inflating the balloon, thereby positioning the stent at the desired location.

U.S. Pat. No. 5,897,529 issued to Ponzi and entitled "Steerable Deflectable Catheter Having Improved Flexibility", is directed to a system for mapping a heart chamber and creating channels in the heart tissue. The system includes a catheter, a computer, a monitor and a pad containing coils. The catheter includes a catheter body, a control handle, an optical fiber, a puller wire, a compression coil, a tip electrode, a ring electrode, temperature sensing means, an electromagnetic sensor and a circuit board. The control handle is attached to a proximal end of the catheter body. A distal end of each of the optical fiber, the puller wire and the compression coil, is located at a distal end of the catheter body. A proximal end of each of the optical fiber, the puller wire and the compression coil, is located at a proximal end of the catheter body.

The tip electrode, the ring electrode and the temperature means are located at the distal end of the catheter body. The circuit board is located within the control handle. The circuit board is attached to the electromagnetic sensor and to the computer. The computer is connected to the monitor and to the coils. The circuit board prevents the system from being used twice, according to a signal received from the electromagnetic sensor. The compression coil provides flexibility to the catheter body.

The coils are located under the patient and generate a magnetic field. The electromagnetic sensor generates a signal in response to the generated magnetic field and the computer determines the position of the electromagnetic sensor and thus the distal end of the catheter body, by processing the signal. The tip electrode and the ring electrode monitor the strength of the electrical signals at a selected location. The temperature sensing means monitor the temperature of the tip electrode.

The tip electrode and the ring electrode allow the user to map the heart chamber. The user simultaneously maps the contours of the heart chamber, the electrical activity of the heart and the displacement of the catheter body, thereby identifying the location of an ischemic tissue. The user then creates channels in the ischemic tissue, via the optical fiber.

U.S. Pat. No. 5,830,222 issued to Makower and entitled "Device, System and Method for Interstitial Transvascular Intervention", is directed to a method for gaining percutaneous access to a diseased vessel through an adjacent intact vessel. Using this method, it is possible to bypass the diseased vessel, such as a coronary artery, through the intact vessel, such as a cardiac vein. The diseased vessel may include an occlusion that restricts the flow. A guide-catheter is advanced through the vena cava into the coronary sinus, within the right atrium of the heart. A transvascular interstitial surgery (TVIS) guide catheter is inserted through the guide-catheter and advanced through the cardiac vein over a first guidewire, to a desired location adjacent the coronary artery.

The TVIS guide-catheter includes a balloon, a TVIS probe and either or both of active orientation detection means and passive orientation detection means. The TVIS probe is a rigid wire, antenna, light guide or energy guide capable of being inserted in tissue. The passive orientation detection means allow radiographic, fluoroscopic, magnetic or sonographic detection of position and orientation of the TVIS probe. The active orientation detection means is a transmitter. A second guidewire is inserted into the coronary artery adjacent the cardiac vein, wherein the second guidewire includes a small receiver to receive a signal emitted by the active orientation detection means. The second guidewire further includes a wire bundle which is capable to return the signal detected by the receiver, to an operator, thereby enabling the operator to determine the position and location of the TVIS probe.

When the orientation of the TVIS guide-catheter is assured, the balloon is inflated against the wall of the cardiac vein, in order to block the flow, stabilize the TVIS guide-catheter within the cardiac vein and dilate the passageway. The TVIS probe, is then advanced through the wall of the cardiac vein into the coronary artery, thereby bypassing the diseased section of the coronary artery.

U.S. Pat. No. 5,489,271 issued to Andersen and entitled "Convertible Catheter", is directed to a percutaneous transluminal coronary angioplasty (PTCA) device, which can be used in either the rapid exchange mode or over-the-wire mode. The device includes a catheter shaft and a hub assembly. The hub assembly is bonded to a proximal end of the catheter shaft and the balloon is bonded to a distal end of the catheter shaft. The hub assembly includes a handle. The catheter shaft includes a guide element, a guidewire lumen, a balloon inflation lumen, and a third lumen in which a nitinol wire permanently resides.

In the rapid exchange mode, a first guidewire extends through the distal end of the guidewire lumen and exits from the catheter shaft, through a side port located distal of the guide element. In this mode, a stylet is located within the guidewire lumen, wherein the distal end of the stylet is proximal to the guide element and the proximal end of the stylet is bonded to the handle. In over-the-wire mode, the guide element is raised into general alignment with the wall of the catheter shaft and the stylet and the first guidewire are replaced by a second guidewire. The second guidewire extends through the guidewire lumen, from the proximal end of the device to the distal end thereof.

U.S. Pat. No. 6,035,856 issued to LaFontaine et al., and entitled "Percutaneous Bypass with Branching Vessel", is directed to a method for performing a bypass on a first occlusion of a branching vessel of the aorta. A coronary artery which includes the first occlusion, and a branching vessel branch out of the aorta. A standard guide-catheter is advanced through the aorta up to the ostium of the branching vessel. An occlusion forming device is advanced through the guide-catheter into the branching vessel, to produce a second occlusion in the branching vessel. The occlusion device includes an elongate portion and a heated balloon.

The occlusion forming device is removed from the aorta through the guide-catheter and a cutting device is advanced through the guide-catheter proximal to the second occlusion. The cutting device includes an elongate member, a steerable guidewire, a proximal occlusion balloon, a distal balloon, a stent, a cutting blade, a first piece of magnetic material and a transmitter. The cutting blade is located distal to the distal balloon, the first piece of the magnetic material is located between the cutting blade and the distal balloon and the transmitter is located within the distal balloon. The distal balloon is located within the stent. The transmitter emits radio frequency signals.

The wall of the branching vessel is cut by employing the cutting blade. The distal balloon is kept in the expanded position, in order to occlude the branching vessel after the branching vessel has been cut. The severed end of the branching vessel is steered toward a region of the coronary artery distal to the first occlusion, by maneuvering the steerable guidewire or by manipulating the first piece of the magnetic material by a second piece of magnetic material, wherein the second piece of magnetic material is located outside the body of the patient.

The true position and the relative position of the transmitter and thus the position of the severed end of the branching vessel, is determined by employing a triangulation and coordinate mapping system. The triangulation and coordinate mapping system includes three reference electrodes which are located outside the body of the patient. Two of the reference electrodes are located on opposite sides of the heart and the third is located on the back. The three reference electrodes are used to triangulate on the transmitter.

When the severed end of the branching vessel is properly positioned, an aperture is formed in the coronary artery distal to the first occlusion, by employing the cutting blade. The severed end of the branching vessel is inserted into the coronary artery through the aperture and the stent is expanded by inflating the distal balloon, thereby attaching the severed end of the branching vessel to the lumen of the coronary artery.

SUMMARY OF THE DISCLOSED TECHNIQUE

It is an object of the disclosed technique to provide a novel method and system for mounting an MPS sensor on a catheter, which overcomes the disadvantages of the prior art.

In accordance with the disclosed technique, there is thus provided a catheter for performing a medical operation on an organic lumen. The catheter includes an elongated member, a medical operational element located at a distal end of the elongated member, an electromagnetic field detector located at the distal end, and a wiring for coupling the electromagnetic field detector with a medical positioning system. The medical positioning system determines the position and orientation of the distal end.

In accordance with another aspect of the disclosed technique, there is thus provided a position and orientation determination system. The position and orientation system includes a guiding catheter, and a guiding catheter electromagnetic field detector located at a guiding catheter distal end of the guiding catheter. The guiding catheter electromagnetic field detector is coupled with the medical positioning system. The medical positioning system determines the position and orientation of the guiding catheter distal end, relative to a reference coordinate system.

In accordance with a further aspect of the disclosed technique, there is thus provided a method for performing a medical operation on an organic lumen. The method includes the procedures of advancing a medical catheter to a desired location within the organic lumen, and coupling an electromagnetic field detector located at a distal end of the medical catheter, with a medical positioning system, by a wiring.

The method further includes the procedures of generating an electromagnetic field by the medical positioning system, detecting the generated electromagnetic field by the electromagnetic field detector, and transmitting a signal respective of the detected electromagnetic field, to the medical positioning system, via the wiring. The method further includes the procedures of determining the position and orientation of the medical catheter distal end, by the medical positioning system, according to the transmitted signal, and performing the medical operation, by activating a medical operational element located at the medical catheter distal end.

In accordance with another aspect of the disclosed technique, there is thus provided a position and orientation determination method. The method includes the procedures of coupling an electromagnetic field detector located at a distal end of a guiding catheter, with a medical positioning system, and generating an electromagnetic field by the medical positioning system.

The method further includes the procedures of detecting the generated electromagnetic field, by the electromagnetic field detector, and transmitting a signal respective of the detected electromagnetic field, by the electromagnetic field detector. The method further includes the procedure of determining the position and orientation of the guiding catheter distal end relative to a reference coordinate system, by the medical positioning system, according to the transmitted signal.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a medical catheter which includes a medical operational element, and an electromagnetic field detector located in proximity of the activation site of the medical operational element. The activation site of the medical operational element is located at a distal end of the medical catheter. The electromagnetic field detector is coupled with a medical positioning system by a wiring. The wiring may be constructed to improve the pushability and traceability of the medical catheter (i.e., the possibility of the medical catheter to follow the path within a human or animal lumen, when pushed through the lumen). A transmitter of the medical positioning system generates an electromagnetic field and the electromagnetic field detector detects the generated electromagnetic field. The electromagnetic field detector sends a signal respective of the detected electromagnetic field to the medical positioning system and the medical positioning system determines the position and orientation of the electromagnetic field detector, and hence the activation site, according to the received signal. It is noted that the term "lumen" refers to an organic tubular structure of the human patient or the operated animal. This lumen is different than the "guidewire lumen" which is a channel in the medical catheter used for passing a guidewire there through.

Figure 1A:
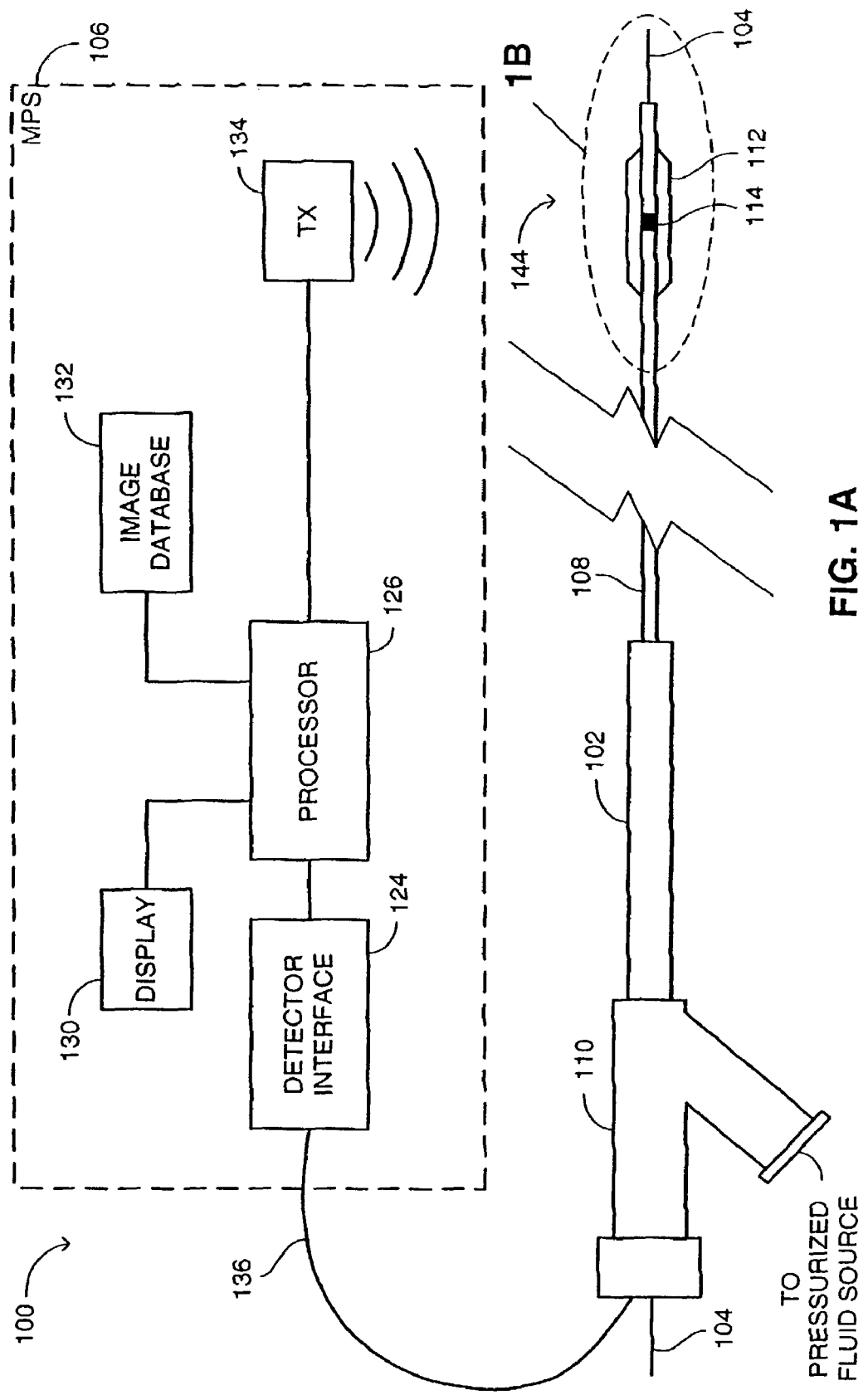
FIG. 1A is a schematic illustration of a system for determining the position and orientation of an activation site of a medical operational element of a medical catheter of the over-the-wire type, constructed and operative in accordance with an embodiment of the disclosed technique.
Figure 1B:
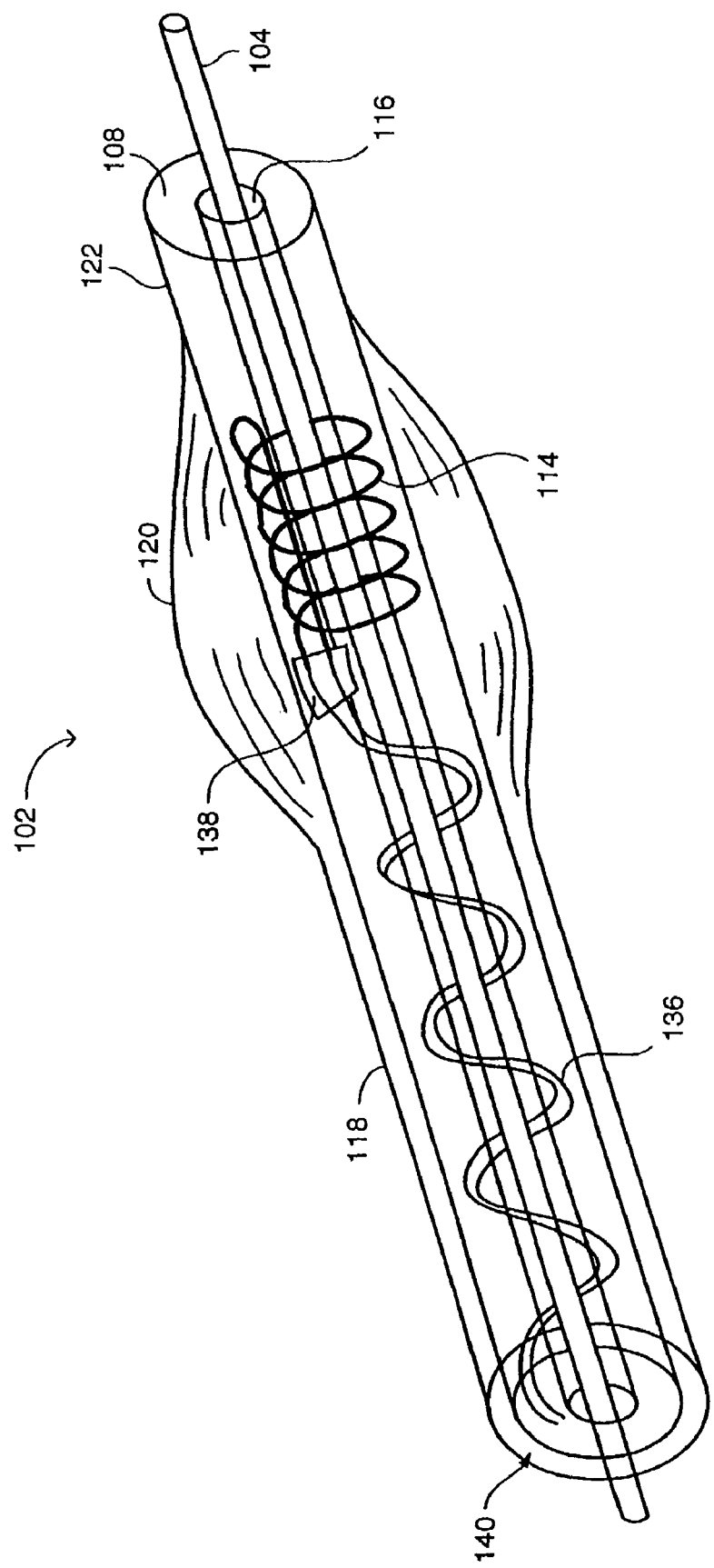
FIG. 1B is a schematic perspective illustration of a distal end of the medical catheter of FIG. 1A.
Figure 1C:
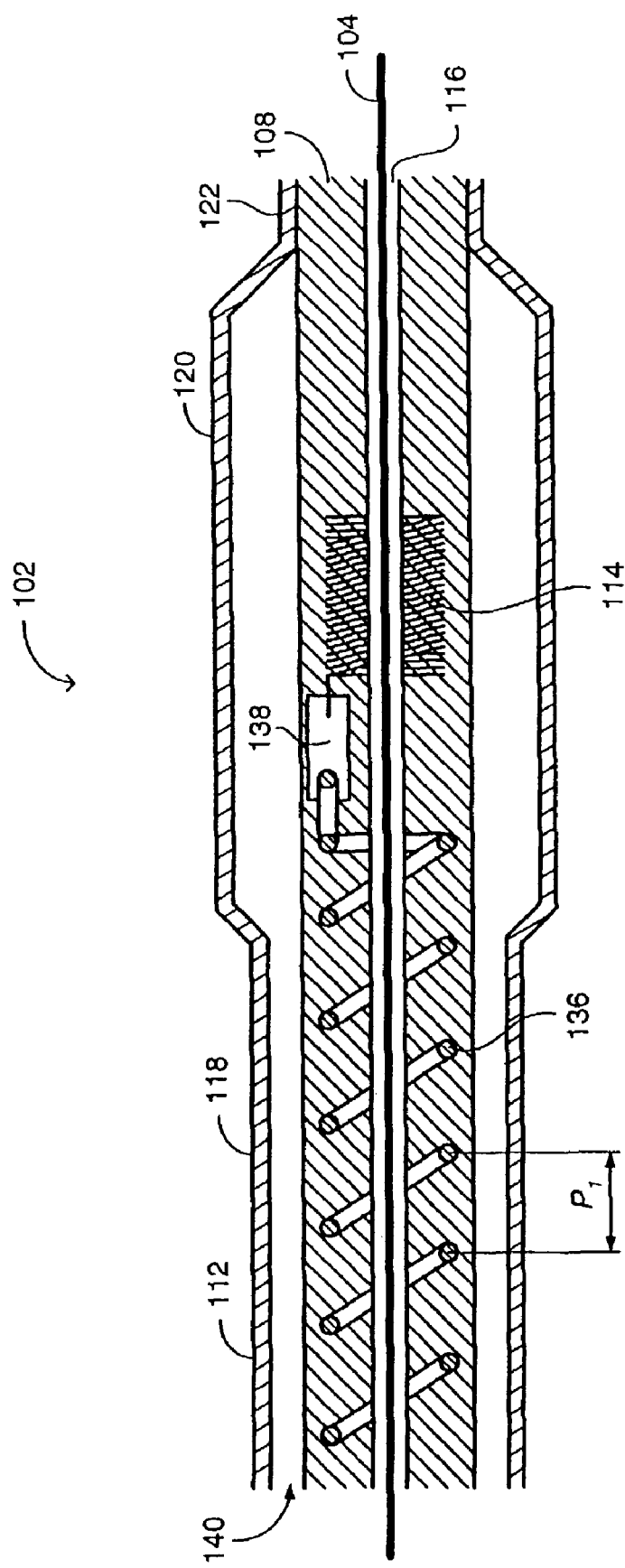
FIG. 1C is a schematic illustration of a longitudinal cross section of the distal end of one example of the medical catheter of FIG. 1A.
Figure 1D:
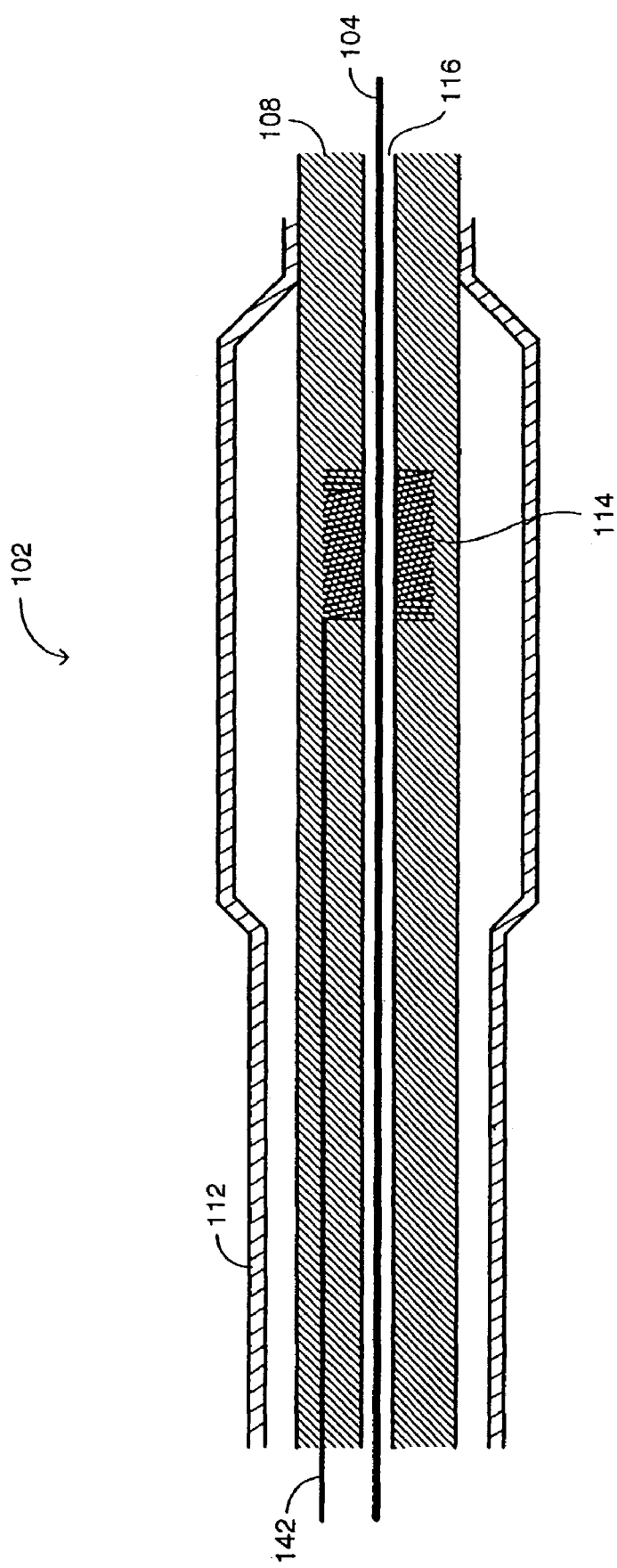
FIG. 1D is a schematic illustration of a longitudinal cross section of the distal end of another example of the medical catheter of FIG. 1A.

Reference is now made to FIGS. 1A, 1B, 1C and 1D. FIG. 1A is a schematic illustration of a system for determining the position and orientation of an activation site of a medical operational element of a medical catheter of the over-the-wire type, generally referenced 100, constructed and operative in accordance with an embodiment of the disclosed technique. FIG. 1B is a schematic perspective illustration of a distal end 144 of the medical catheter of FIG. 1A. FIG. 1C is a schematic illustration of a longitudinal cross section of the distal end of one example of the medical catheter of FIG. 1A. FIG. 1D is a schematic illustration of a longitudinal cross section of the distal end of another example of the medical catheter of FIG. 1A.

System 100 includes a medical catheter 102, a guidewire 104 and a medical positioning system (MPS) 106. Medical catheter 102 includes an elongated member 108, a manifold 110, a medical operational element 112 and an electromagnetic field detector 114. The medical operational element can include a lumen intervention element, a lumen diagnostic element, a lumen imaging element, and the like. Elongated member 108 is made of a substantially flexible material, such as poly ether ether ketone (PEEK), polyethylene (PE), nylon, polyurethane, polyvinyl chloride (PVC), polyethylene terephthalate (PET), Pebax®, polyimide, metal (either solid or coiled), such as nitinol, stainless steel, hypotube (i.e., an ultra low diameter and ultra thin walled tube), and the like. Elongated member 108 has a substantially circular cross section and includes a guidewire lumen 116. Manifold 110 is located at a proximal end of medical catheter 102 and medical operational element 112 is located at a distal end of medical catheter 102.

Medical operational element 112 is an element for performing medical operations in the lumen, such as modifying the characteristics of the lumen, or diagnosing the lumen, such as obtaining an image of the lumen. The characteristics of the lumen can be modified by performing a medical procedure thereon, such as percutaneous transluminal coronary angioplasty (PTCA), percutaneous transluminal angioplasty (PTA), vascularizing the lumen, severing a portion of the lumen or a plaque there within (e.g., atherectomy), providing a suture to the lumen, increasing the inner diameter of the lumen (e.g., by a balloon, a self expanding stent, a stent made of a shape memory alloy (SMA), or a balloon expanding stent) and maintaining the increased diameter by implanting a stent.

Medical operational element 112 can be further used to deliver substances to the lumen. For example, medical operational element 112 can be used to deliver a pharmaceutical substance to a selected site within the lumen, such as for inhibiting angiogenesis of cancerous cells, inhibiting metastasis, stimulating local hormonal activity of tissue cells and stimulating healing following a trauma. Medical operational element 112 can be further used for killing selected cells (either cancerous or non-cancerous) at the activation site of medical operational element 112 or in the vicinity thereof, by irradiating the cells with a radioactive substance, electric current, laser, or subjecting the cells to a cryogenic fluid, and the like. Medical operational element 112 can be further include, or be used for deployment of, a device within the lumen. Such a device can be for example, a valve (e.g., mitral valve, sphincter), suturing device, implant, biological marker, radiopaque marker, substance delivery device, imaging device, diagnostic device, miniature camera, infrared camera, optical coherence tomography (OCT), magnetic resonance imaging (MRI), ultrasound, sensor, such as pressure sensor, temperature sensor, pH sensor, and the like. The sensor can be in form of a passive ultrasonic transducer, which transmits signals bearing the value of the detected parameter (pressure, temperature, pH etc.), in response to an ultrasonic wave directed from an external source toward the sensor. Medical operational element 112 can also be used to perform a valvuloplasty operation (i.e., repair of an organic or an artificial valve). The lumen can be a portion of the vascular system, ureter, urethra, brain vessels, coronary vessels, vas deferens, lumens of the liver, kidney, lung (e.g., trachea and bronchus), digestive system, gal bladder, prostate gland, urogenital system, and the like. The lumen can be in the body of a human being as well as an animal.

Medical operational element 112 can be an expansion unit such as a balloon, stent, balloon expanding stent, an ablation unit such as laser, cryogenic fluid unit, electric impulse unit, cutting balloon, rotational atherectomy unit (i.e., rotablator), directional atherectomy unit, transluminal extraction unit, a substance delivery unit such as coated stent, drug delivery balloon, brachytherapy unit, and the like.

The balloon expanding stent unit includes a stent which is located around a balloon. When the balloon is inflated, the stent expands. The cutting balloon unit includes a balloon having a plurality of blades on the periphery thereof, along the longitudinal axis of the elongated member. The cryogenic fluid unit includes a fluid delivery lumen through which a fluid at a substantially low temperature is delivered to a desired site of the lumen. The electric impulse unit includes two electrical conductors. An electrical arc generated at the tip of the electrical conductors ablates the desired site of the lumen.

The rotablator includes a diamond coated tip which is coupled with an external motor via a flexible shaft. The flexible shaft rotates the diamond coated tip at a substantially high speed, wherein the diamond coated tip grinds calcified plaque which is formed on the inner wall of the lumen. The ground material enters the circulation.

The directional atherectomy unit includes a cutter and a balloon. The cutter is coupled with an external motor via a flexible shaft. The balloon pushes the cutter toward the sidewall opposite to the balloon, thereby allowing the cutter to cut the calcified plaque. The calcified particles are pumped out through the medical catheter. The transluminal extraction unit includes a cutter which is coupled with an external motor via a flexible shaft. The motor rotates the cutter, wherein the cutter cuts the calcified plaque and the calcified particles are pumped out through the medical catheter.

The coated stent is coated with a pharmaceutical substance, wherein the substance is released into a desired region of the lumen, when the coated stent is installed in the lumen. The drug delivery balloon is a balloon which is coupled to a source of a pharmaceutical substance, via a drug delivery lumen. The pharmaceutical substance exits the balloon through a plurality of micropores. The brachytherapy unit includes a substance delivery lumen, through which radioactive palettes are delivered to a desired site within the lumen. The radioactive palettes remain at the desired site for a prescribed time and then are scavenged out through the substance delivery lumen. Thus, a prescribed dose of radiation is delivered to the desired site of the lumen.

In the example set forth in FIG. 1A, medical catheter 102 is a balloon type catheter. Hence, medical operational element 112 includes a tube portion 118 and a balloon portion 120. Each of tube portion 118 and balloon portion 120 is made of a substantially thin and flexible material, such as polyamide (e.g., nylon), and the like. Balloon portion 120 can be made either of a compliant material, semi-complaint material, or a non-compliant material. A compliant balloon continuously expands as higher pressures are applied thereto. A non-compliant balloon expands up to a predetermined diameter which is designed therein, and ceases to expand above this predetermined diameter, even if the applied pressure continues to rise. The expansion rate of a semi-compliant balloon drops as the pressure rises. Balloon portion 120 is located at a distal end of tube portion 118. A proximal end of tube portion 118 is coupled with a pressurized fluid source (not shown), via manifold 110 and a circumferential fluid lumen 140. Circumferential fluid lumen 140 runs along the entire length of medical catheter 102. The pressurized fluid source can be an ampoule such as a syringe, and the like, which contains a biocompatible fluid. The pressurized fluid source can be provided with a sensor to detect a property of the fluid, such as pressure, temperature, pH, and the like.

A distal end 122 of balloon portion 120 is coupled with an outer wall (not shown) of elongated member 108, by methods known in the art, such as by an adhesive, ultrasonic welding, heat bonding, by applying infrared radiation, radio frequency (RF) radiation, laser, ultraviolet (UV) radiation, and the like. The circumference of balloon portion 120 is larger than that of tube portion 118. In an uninflated state, balloon portion 120 folds around elongated member 108. When fluid flows under pressure from the pressurized fluid source into tube portion 118, balloon portion 120 unfolds and expands. When the pressure fluid source is unpressurized or the fluid is withdrawn from tube portion 118, the interstitial fluid in the lumen forces balloon portion 120 to fold around elongated member 108.

Electromagnetic field detector 114 is an electric conductor formed into a coil. Electromagnetic field detector 114 is embedded within elongated member 108, such that guidewire lumen 116 passes through the winding of electromagnetic field detector 114. Alternatively, the electromagnetic field detector can be sufficiently small to be entirely embedded within a lateral portion of the wall of the elongated member, adjacent to guidewire lumen 116. In the example set forth in FIGS. 1A, 1B and 1C, electromagnetic field detector 114 is embedded within elongated member 108, in such a location that when balloon portion 120 expands, balloon portion 120 encompasses electromagnetic field detector 114. However, it is noted that electromagnetic field detector 114 can be located either distal or proximal to balloon portion 120. Furthermore, electromagnetic field detector 114 can be made of a radio-paque material or coated with such a material, thereby being detectable by an imaging device, such as radiographic, fluoroscopic, magnetic, sonographic device, and the like.

With reference to FIG. 1A, MPS 106 includes a detector interface 124, a processor 126, a display 130, an image database 132 and a transmitter 134. MPS 106 is located outside the body of a patient (not shown). Processor 126 is coupled with detector interface 124, display 130, image database 132 and with transmitter 134. Image database 132 includes a plurality of images of a lumen (not shown) of the patient, wherein each image is associated with a set of position and orientation coordinates, in a reference coordinate system.

Two ends (not shown) of electromagnetic field detector 114 are coupled with two distal ends (not shown) of a wiring 136, via a flexible printed circuit board (PCB) 138. However, it is noted that the two ends of electromagnetic field detector 114 can be coupled with the two distal ends of wiring 136, directly, (e.g., by soldering or conductive adhesion) in which case flexible PCB 138 can be disposed of. Proximal ends (not shown) of wiring 136 are coupled with detector interface 124. For a more elaborate description of an MPS, confer U.S. Pat. No. 6,233,476 mentioned above.

Wiring 136 is made of an electric conductor, such as copper, gold, silver, and the like. Wiring 136 is spirally embedded within elongated member 108, such that guidewire lumen 116 is surrounded by wiring 136. It is noted that the term "spiral" includes, inter alia, helical forms. The pitch of wiring 136 is referenced by $P_1$. Wiring 136 is spirally embedded within elongated member 108 at pitch $P_1$, in a section (not shown) of elongated member 108 which starts from the two distal ends of electromagnetic field detector 114 and ends at manifold 110. Alternatively, wiring 136 is spirally embedded within the section of elongated member 108, at a plurality of different pitches. Further alternatively, a portion of wiring 136 proximal to electromagnetic field detector 114 is spirally embedded within elongated member 108 at pitch $P_1$, and the rest of wiring 136 is embedded within elongated member 108 along a substantially straight line. Alternatively, at least one portion of wiring 136 is spirally embedded within elongated member 108 and at least another portion of wiring 136 is embedded within elongated member 108, along a substantially straight line. With reference to FIG. 1D, a wiring 142 is embedded within elongated member 108, along a substantially straight line.

According to one aspect of the invention the spiral winding of wiring 136 modifies certain mechanical properties of elongated member 108, such as improving the pushability and trackability of medical catheter 102 within the lumen of the patient (i.e., reducing the tendency of medical catheter 102 to buckle when pushed within the lumen and increasing the ability of the medical catheter to follow the vessel path), increasing the elasticity of elongated member 108 (i.e., increasing the tendency of elongated member 108 to return to the original shape, after being deformed), increasing the modulus of elasticity of elongated member 108 (i.e., increasing the mechanical stress in either compression or tension, which is required to deform elongated member 108 by a certain amount), increasing the coefficient of rigidity of elongated member 108 (i.e., increasing the mechanical shear stress which is required to twist elongated member 108 by a certain angle), affecting the flexibility or resilience of elongated member 108, and the like. It is further noted that the mechanical properties of wiring 136, also modifies the mechanical properties of elongated member 108. Wiring 136 can be coated with a coating that provides electrical insulation, or electrical shielding, as well as mechanical protection to wiring 136.

Following is a description of operation of system 100. Initially, the user (usually a physician) inserts a guiding catheter (not shown) into the lumen, such that a distal end of the guiding catheter reaches a desired location within the lumen. The physician can view an image of the guiding catheter by employing an imaging device, such as radiographic, fluoroscopic, magnetic, sonographic device, and the like. The physician inserts guidewire 104 in the guiding catheter and maneuvers a distal end (not shown) of guidewire 104 past the guiding catheter through the lumen, by observing an image of guidewire 104 in an imaging device, such as radiographic, fluoroscopic, magnetic, sonographic device, and the like Guidewire 104 is a "small-diameter" guidewire, referred to in the Background of the Disclosed Technique, hereinabove. The physician, then inserts a proximal end (not shown) of guidewire 104 in the distal end of medical catheter 102, and passes medical catheter 102 over guidewire 104, into the lumen, such that the proximal end of guidewire 104 usually exits a proximal end (not shown) of medical catheter 102. This mode of operation is known in the art as "over-the-wire". Alternatively, no guidewire is employed in the procedure, in which case the physician passes the medical catheter out through the distal end of the guiding catheter, until the distal end of the medical catheter reaches a selected location within the lumen. Transmitter 134 produces a rotating magnetic and electric field of fixed strength, orientation and frequency.

Electromagnetic field detector 114 produces a signal according to the position and orientation thereof, relative to transmitter 134 and electromagnetic field detector 114 provides this signal to detector interface 124, via wiring 136. Processor 126 receives the signal via detector interface 124 and processor 126 determines the position and orientation of electromagnetic field detector 114 relative to the reference coordinate system, according to the received signal.

Processor 126 retrieves an image of the lumen from image database 132 and superimposes a representation of medical operational element 112 on the retrieved image, according to the determined position and orientation. Processor 126 produces a video signal respective of the superimposed image to display 130 and display 130 produces the representation of medical operational element 112, superimposed on the image of the lumen. When the physician is assured that medical operational element 112 is located at the desired site within the lumen, by viewing the superimposed image on display 130, the physician can commence the medical operation on the lumen.

Various electronic devices which are present in the operation room, may emit electromagnetic radiation which may interfere with the signal which the electromagnetic field detector transmits to the MPS, via the wiring. In this case, necessary hardware or software has to be incorporated with the system, in order to reduce the effect of these interfering signals.

For example, at least a portion of the electromagnetic field detector can be covered with a shielding of such thickness and material (e.g., a conductive foil, a wire mesh), to selectively cancel out these interfering signals, while allowing the signal from the transmitter of the MPS, to reach the electromagnetic field detector. This electrical shielding of the wiring acts as a Faraday cage within a predetermined range of frequencies.

Figure 2:
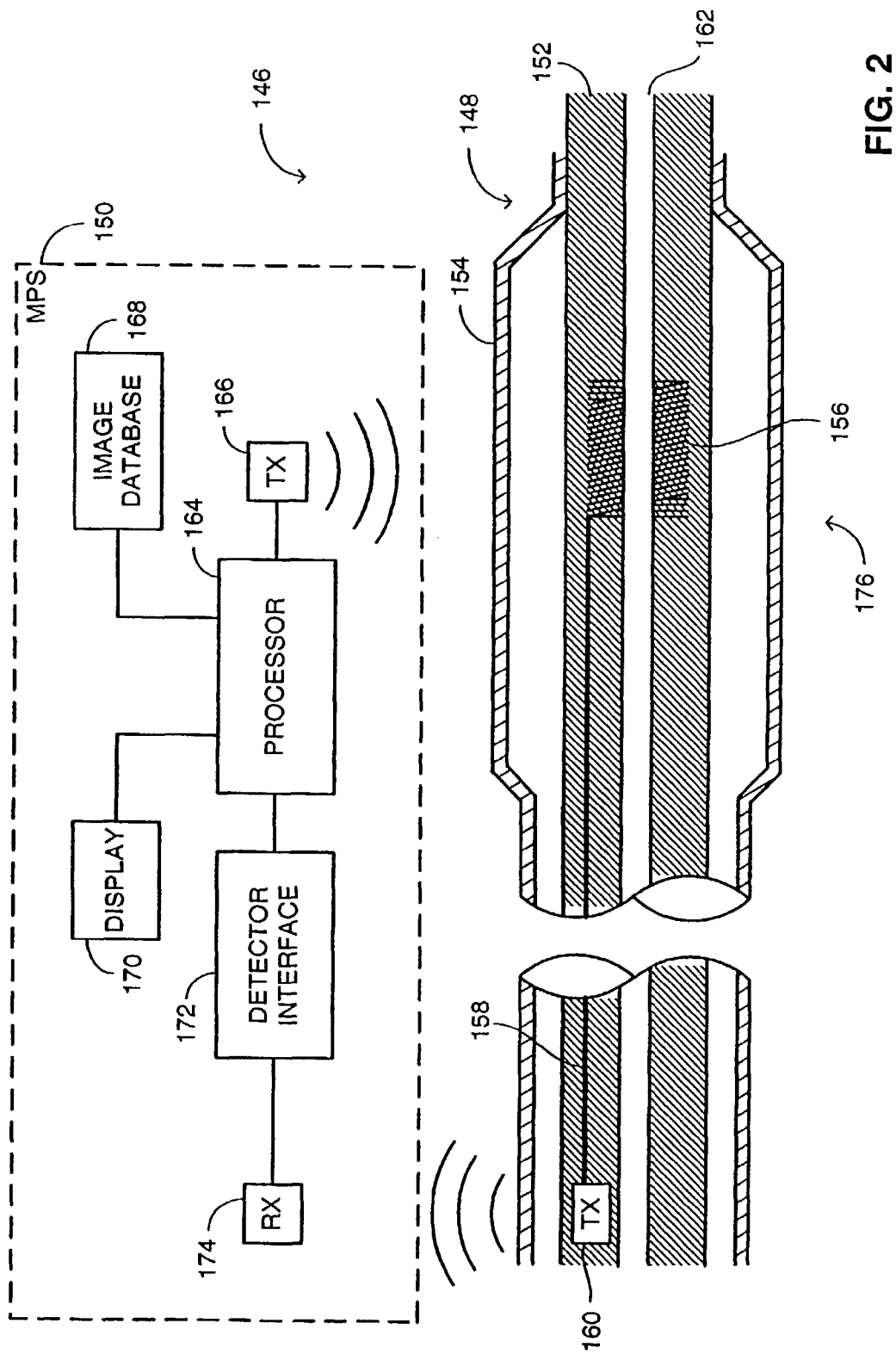
FIG. 2 is a schematic illustration of a system for determining the position and orientation of an activation site of a medical operational element of a medical catheter, constructed and operative in accordance with another embodiment of the disclosed technique.

Reference is now to FIG. 2, which is a schematic illustration of a system for determining the position and orientation of an activation site of a medical operational element of a medical catheter, generally referenced 146, constructed and operative in accordance with another embodiment of the disclosed technique. System 146 includes a medical catheter 148 and an MPS 150. FIG. 2 illustrates the distal portion of medical catheter 148, which is typically about 20 cm long.

Medical catheter 148 includes an elongated member 152, a medical operational element 154, an electromagnetic field detector 156, a wiring 158 and a transmitter 160. Elongated member 152 includes a guidewire lumen 162. MPS 150 includes a processor 164, a transmitter 166, an image database 168, a display 170, a detector interface 172 and a receiver 174.

Wiring 158 is similar to wiring 136 (FIG. 1B), as described herein above and is embedded within elongated member 152. Medical operational element 154 and electromagnetic field detector 156 are located at a distal end 176 of medical catheter 148. Electromagnetic field detector 156 is embedded within elongated member 152, and encompasses guidewire lumen 162. Transmitter 160 is embedded within elongated member 152 and located proximal to distal end 176. Alternatively, the transmitter can be located at a manifold similar to manifold 110 (FIG. 1A) or anywhere along elongated member 152 or external thereto. One end of wiring 158 is coupled with electromagnetic field detector 156 and the other end thereof is coupled with transmitter 160. The length of wiring 158 is much shorter than that of elongated member 152, such that wiring 158 occupies a relatively short section of the distal portion of elongated member 152 (usually about 20 cm).

Processor 164 is coupled with transmitter 166, image database 168, display 170 and with detector interface 172. Receiver 174 is coupled with detector interface 172. Transmitter 166 transmits an electromagnetic wave which is received by electromagnetic field detector 156 and electromagnetic field detector 156 sends a signal respective of the position and orientation of distal end 176 to transmitter 160, via wiring 158. Transmitter 160 transmits this signal to receiver 174 and processor 164 determines the position and orientation of distal end 176, according to a signal received from detector interface 172.

It is noted that wiring 158 modifies the mechanical properties of the distal portion of elongated member 152, as described herein above in connection with FIG. 1B, such as pushability and trackability. Alternatively, the electromagnetic field detector can be located external to the elongated member (as described herein below in connection with FIG. 3). Further alternatively, the wiring can be wound around the elongated member. Further alternatively, the transmitter can be located external to the elongated member. It is further noted that medical catheter 148 can be of over-the-wire type, as well as rapid exchange type.

Figure 3:
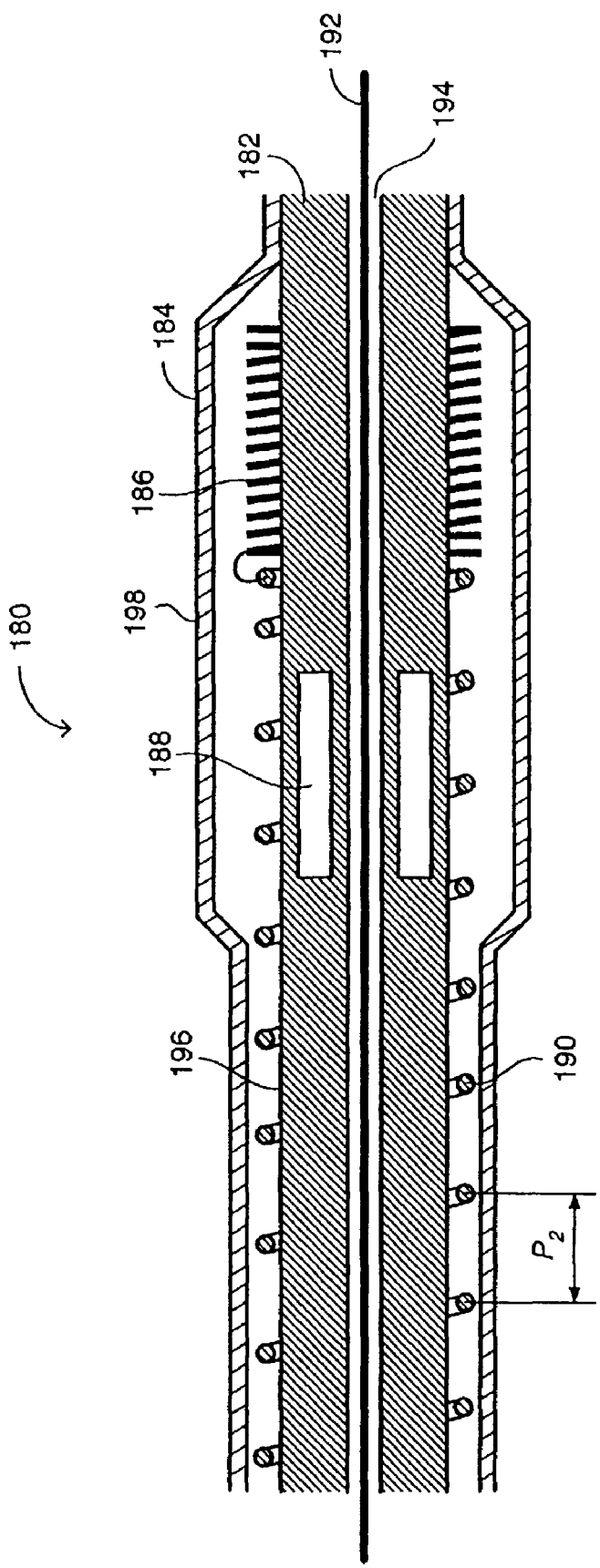
FIG. 3 is a schematic illustration of a longitudinal cross section of a distal end of a medical catheter, constructed and operative in accordance with a further embodiment of the disclosed technique.

Reference is now made to FIG. 3, which is a schematic illustration of a longitudinal cross section of a distal end of a medical catheter, generally referenced 180, constructed and operative in accordance with a further embodiment of the disclosed technique. Medical catheter 180 includes an elongated member 182, a medical operational element 184, an electromagnetic field detector 186, a marker 188 and a wiring 190. A guidewire 192 can pass through a guidewire lumen 194 within elongated member 182.

Elongated member 182 and medical operational element 184 are similar to elongated member 108 (FIG. 1A) and medical operational element 112, respectively. Electromagnetic field detector 186 is made of a conductor which is wound around an outer wall 196 of elongated member 182, at an activation site of medical operational element 184, such as a balloon portion 198. Marker 188 is made of a radiopaque material, such as platinum, iridium, gold, tungsten, stainless steel, silver, composite material, and the like, which can be detected by an imaging device, such as radiographic, fluoroscopic, magnetic, sonographic device, and the like. Marker 188 is embedded within elongated member 182 at the activation site of medical operational element 184, such as balloon portion 198. Alternatively, marker 188 is located on outer wall 196 (i.e., outer wall 196 is coated with marker 188).

Wiring 190 is wound around outer wall 196 at a pitch $P_2$. For this purpose, spiral grooves (not shown) can be formed on outer wall 196, by a laser, mechanical engraving, chemical etching, molding; injection; and extrusion, and the like, and wiring 190 is then placed in the spiral grooves. Electromagnetic field detector 186 and wiring 190 are coated with a protective coating, in order to provide electrical insulation and mechanical protection to electromagnetic field detector 186 and to wiring 190 and mechanically couple electromagnetic field detector 186 and wiring 190 to outer wall 196. Alternatively, electromagnetic field detector 186 and wiring 190 are enclosed by a heat-shrinkable material. Two ends (not shown) of electromagnetic field detector 186 are coupled with two distal ends (not shown) of wiring 190. Two proximal ends (not shown) of wiring 190 are coupled with an MPS similar to MPS 106 (FIG. 1A). Further alternatively, the wiring is coupled to the outer wall of the elongated member, along a substantially straight line (not shown). Alternatively, the wiring is wound around the outer wall of the elongated member, at either a constant pitch or a variable pitch along the length of the elongated member. Further alternatively, at least one portion of the wiring is substantially straight and at least another portion is spiral.

Figure 4:
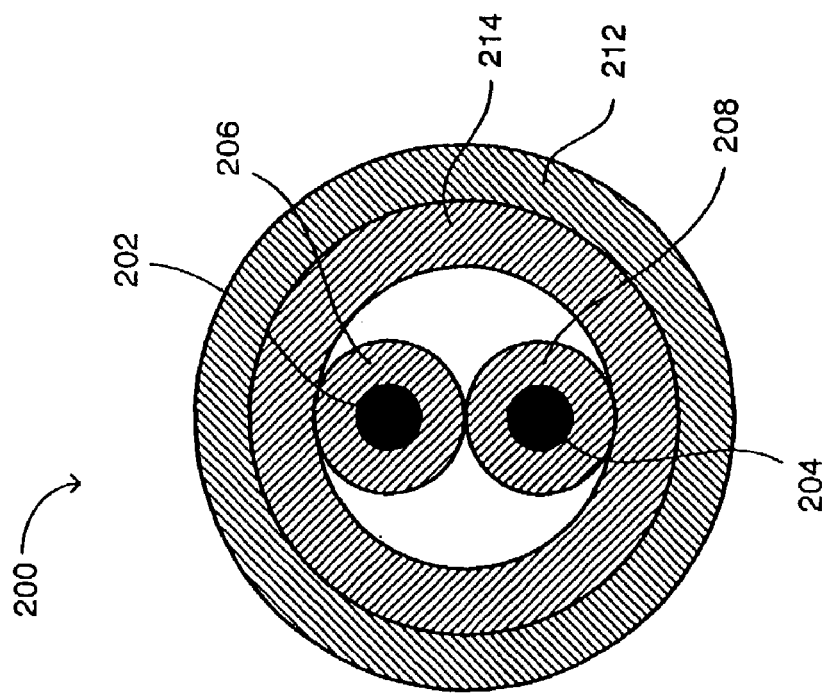
FIG. 4 is a schematic illustration of a lateral cross section of the wiring of a system for determining position and orientation, such as shown in FIG. 1A, in a twisted pair formation, constructed and operative in accordance with another embodiment of the disclosed technique.

Reference is now made to FIG. 4, which is a schematic illustration of a lateral cross section of the wiring of a system for determining position and orientation, such as shown in FIG. 1A, in a twisted pair formation, generally referenced 200, constructed and operative in accordance with another embodiment of the disclosed technique. It is noted that the cross sectional proportions of the different elements in FIG. 4 and all other Figures accompanying this disclosure are not intended to illustrate the actual dimensions or proportions and are exaggerated for the sake of clarity. Wiring 200 includes electrical conductors 202 and 204, electrical insulations 206, 208 and 212 and an electrical shielding 214. Electrical shielding 214 is a shielding layer similar to the shielding of the electromagnetic field detector described above, and provides electrical shielding to electrical conductors 202 and 204. Alternatively, electrical shielding 214 can be a fluid layer which blocks electromagnetic waves in predetermined frequency ranges. Further alternatively, a circumferential fluid lumen similar to circumferential fluid lumen 140 (FIG. 1B), can function as an electrical shielding for the wiring, or an electromagnetic field detector similar to electrical field detector 114. Further alternatively, each of electrical conductors 202 and 204 can be hollow, wherein the hollow space is filled with a fluid. This fluid can be employed for transmitting signals or for other medical intervention purposes.

Electrical conductors 202 and 204 are enclosed within electrical insulations 206 and 208, respectively. Distal ends (not shown) of electrical conductors 202 and 204 are coupled with two ends (not shown) of an electromagnetic field detector (not shown), similar to electromagnetic field detector 114 (FIG. 1C). Proximal ends (not shown) of electrical conductors 202 and 204 are coupled with an MPS (not shown) similar to MPS 106 (FIG. 1A). Electrical conductors 202 and 204 together with electrical insulations 206 and 208, are twisted together between the coupling to the electromagnetic field detector and the coupling to the MPS. Thus, electrical conductors 202 and 204 together with electrical insulations 206 and 208, form a twisted pair (not shown). Electrical shielding 214 encloses electrical conductors 202 and 204 and electrical insulations 206 and 208. Electrical insulation 212 encloses electrical conductors 202 and 204, electrical insulations 206 and 208 and electrical shielding 214.

Figure 5:
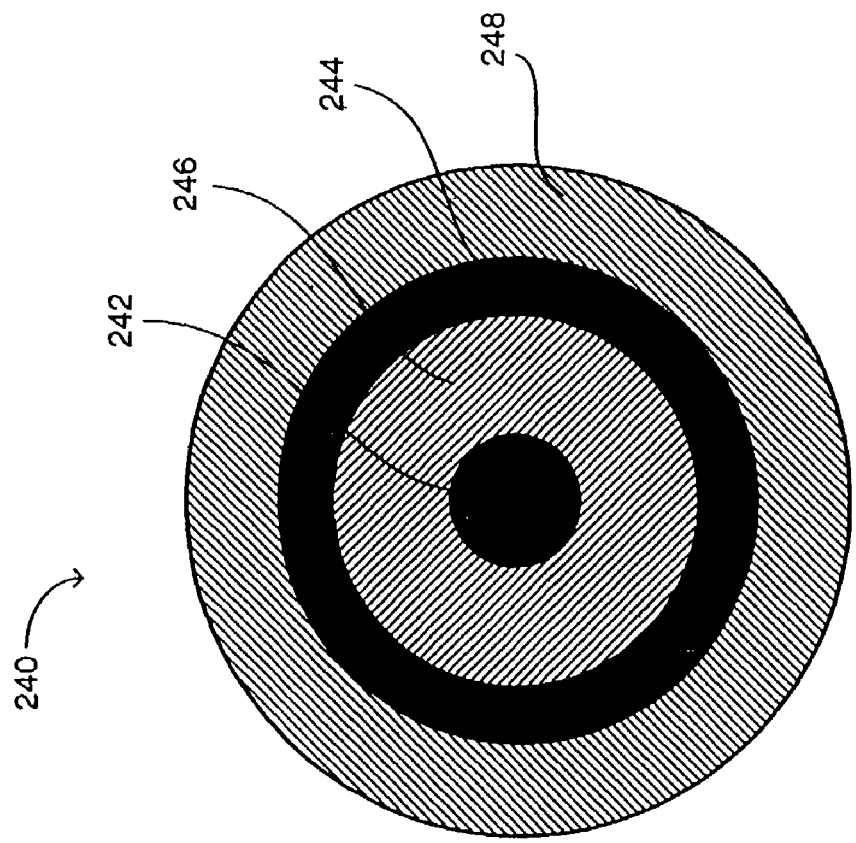
FIG. 5 is a schematic illustration of a lateral cross section of the wiring of a system for determining position and orientation, such as shown in FIG. 1A, in a coaxial formation, constructed and operative in accordance with a further embodiment of the disclosed technique.

Reference is now made to FIG. 5, which is a schematic illustration of a lateral cross section of the wiring of a system for determining position and orientation, such as shown in FIG. 1A, in a coaxial formation, generally referenced 240, constructed and operative in accordance with a further embodiment of the disclosed technique. Wiring 240 includes electrical conductors 242 and 244 and electrical insulations 246 and 248. Electrical insulation 246 encloses electrical conductor 242. Electrical conductor 244 has a substantially annular cross section and thus, encompasses electrical conductor 242 and electrical insulation 246. Electrical insulation 248 encompasses electrical conductors 242 and 244 and electrical insulation 246. Distal ends (not shown) of electrical conductors 242 and 244 are coupled with two ends (not shown) of an electromagnetic field detector (not shown), similar to electromagnetic field detector 114 (FIG. 1C). Proximal ends (not shown) of electrical conductors 242 and 244 are coupled with an MPS (not shown) similar to MPS 106 (FIG. 1A). Thus, electrical conductors 242 and 244 together with electrical insulations 246 and 248, form a coaxial cable.

Figure 6:
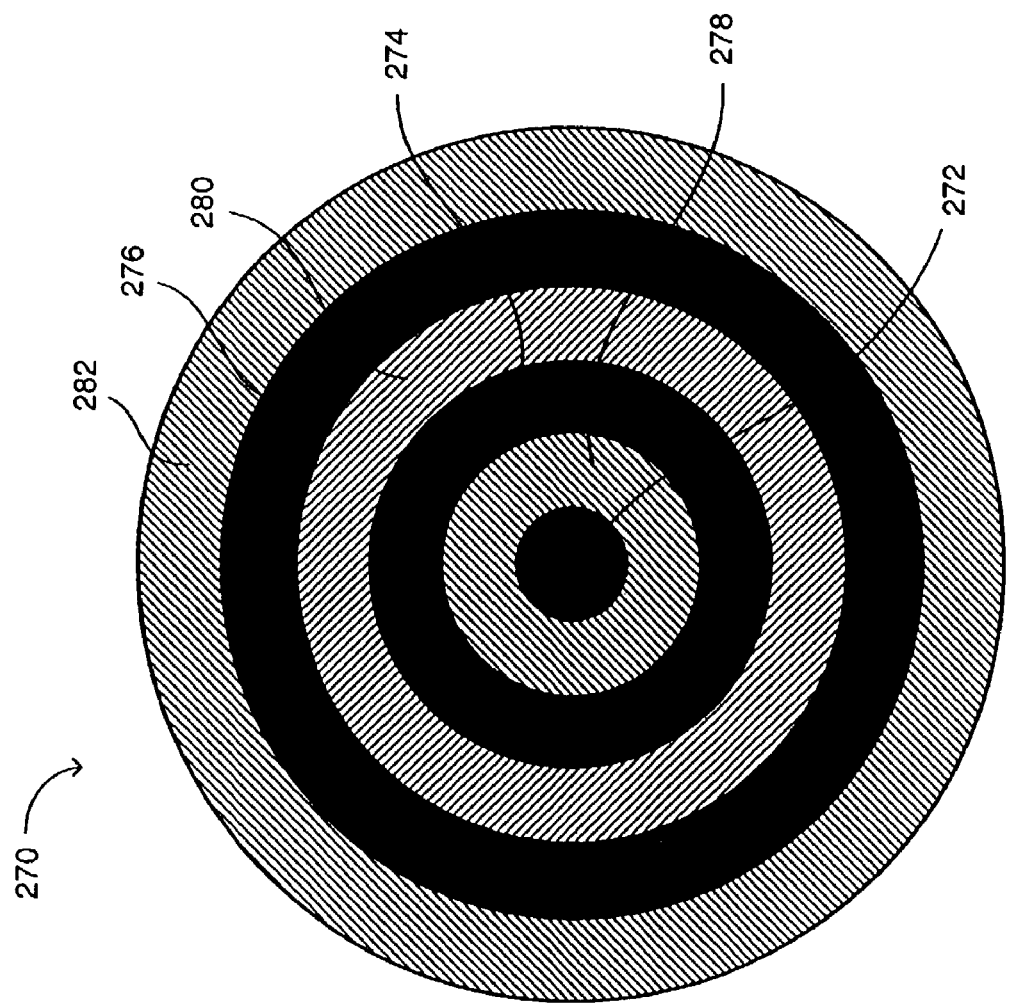
FIG. 6 is a schematic illustration of a lateral cross section of the wiring of a system for determining position and orientation, such as shown in FIG. 1A, in a triaxial formation, constructed and operative in accordance with another embodiment of the disclosed technique.

Reference is now made to FIG. 6, which is a schematic illustration of a lateral cross section of the wiring of a system for determining position and orientation, such as shown in FIG. 1A, in a triaxial formation, generally referenced 270, constructed and operative in accordance with another embodiment of the disclosed technique. Wiring 270 includes electrical conductors 272 and 274, electrical shielding 276 and electrical insulations 278, 280 and 282. Electrical shielding 276 is made of a conductive material, which operates as a Faraday cage and provides electrical shielding to electrical conductors 272 and 274.

Electrical insulation 278 encompasses electrical conductor 272. Electrical conductor 274 has a substantially annular cross section and thus, encompasses electrical conductor 272 and electrical insulation 278. Electrical insulation 280 encompasses electrical conductors 272 and 274 and electrical insulation 278.

Electrical shielding 276 encompasses electrical conductors 272 and 274 and electrical insulations 278 and 280. Electrical insulation 282 encompasses electrical conductors 272 and 274, electrical insulations 278 and 280 and electrical shielding 276. Distal ends (not shown) of electrical conductors 272 and 274 are coupled with two ends (not shown) of an electromagnetic field detector (not shown), similar to electromagnetic field detector 114 (FIG. 1C). Proximal ends (not shown) of electrical conductors 272 and 274 are coupled with an MPS (not shown) similar to MPS 106 (FIG. 1A). Thus, electrical conductors 272 and 274 together with electrical insulations 278, 280 and 282 and electrical shielding 276, form a triaxial cable.

Figure 7A:
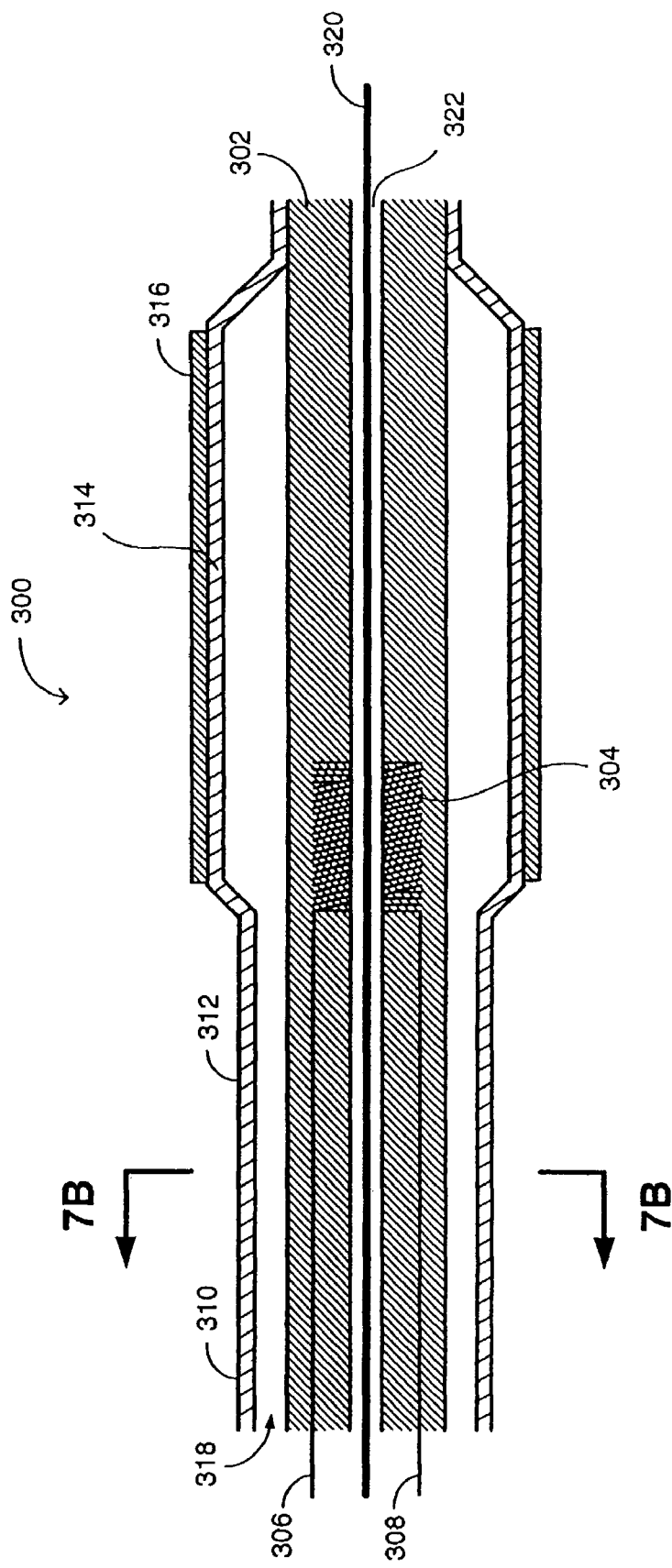
FIG. 7A is a schematic illustration of a longitudinal cross section of the distal end of the medical catheter of a system for determining position and orientation, such as shown in FIG. 1A, constructed and operative in accordance with a further embodiment of the disclosed technique.
Figure 7B:
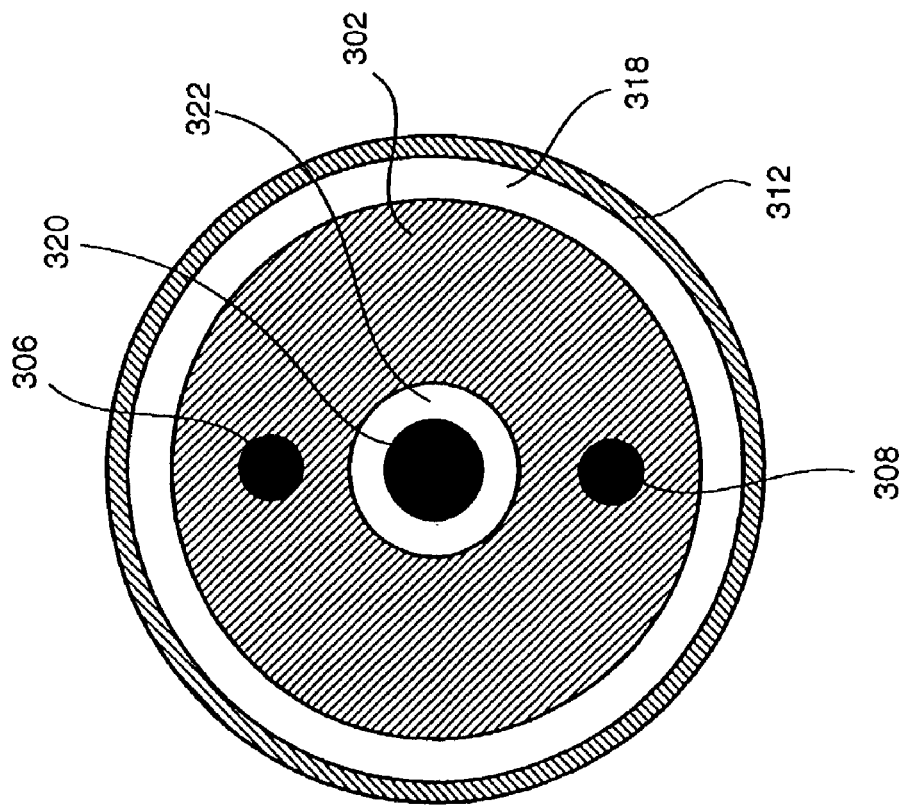
FIG. 7B is a lateral cross section of the medical catheter of FIG. 7A.

Reference is now made to FIGS. 7A and 7B. FIG. 7A is a schematic illustration of a longitudinal cross section of the distal end of the medical catheter of a system for determining position and orientation, such as shown in FIG. 1A, generally referenced 300, constructed and operative in accordance with a further embodiment of the disclosed technique. FIG. 7B is a lateral cross section of the medical catheter of FIG. 7A.

Medical catheter 300 includes an elongated member 302, an electromagnetic field detector 304, electrical conductors 306 and 308 and a medical operational element 310. Elongated member 302 and electromagnetic field detector 304 are similar to elongated member 108 (FIG. 1A) and electromagnetic field detector 114 (FIG. 1C), respectively. In the example set forth in FIG. 7A, medical catheter 300 is a balloon-stent type catheter. Therefore, medical operational element 310 includes a tube portion 312, a balloon portion 314 and a stent 316. Tube portion 312 and balloon portion 314 are similar to tube portion 118 (FIG. 1C) and balloon portion 120, respectively. Tube portion 312 is coupled with a pressurized fluid source (not shown), via a fluid lumen 318. A guidewire 320 can be passed through a guidewire lumen 322 within elongated member 302.

Electromagnetic field detector 304 is embedded within elongated member 302, in a manner similar to the one described herein above in connection with electromagnetic field detector 114 (FIG. 1C). Distal ends (not shown) of electrical conductors 306 and 308 are coupled with two ends (not shown) of electromagnetic field detector 304. Proximal ends (not shown) of electrical conductors 306 and 308 are coupled with an MPS (not shown), similar to MPS 106 (FIG. 1A).

Each of electrical conductors 306 and 308 can be encompassed within an electrical insulation (not shown). Alternatively, each of electrical conductors 306 and 308 can be encompassed within an electrical shielding (not shown). Further alternatively, an electrical shielding can encompass each of electrical conductors 306 and 308 and the respective electrical insulation. Alternatively, an electrical insulation can encompass each of electrical conductors 306 and 308 and the respective electrical shielding.

Electrical conductors 306 and 308 are substantially located on the same diametrical line of elongated member 302 and equally spaced from the center of elongated member 302. In other words, electrical conductor 306 is embedded within elongated member 302 along a first path and electrical conductor 308 is embedded within elongated member 302 along a second path. These first and second paths substantially lie on a plane, whereby the plane substantially passes through the longitudinal axis of elongated member 302. It is noted that electrical conductors 306 and 308 can modify the mechanical properties of elongated member 302, as described herein above in connection with wiring 136 (FIG. 1C).

Stent 316 is an expandable type of stent as known in the art, such as a wire mesh, a cylinder which includes a longitudinal cut, and the like. A fluid flowing from the pressurized fluid source to tube portion 312, causes balloon portion 314 to expand and the expansion of balloon portion 314 causes stent 316 to expand.

Figure 8:
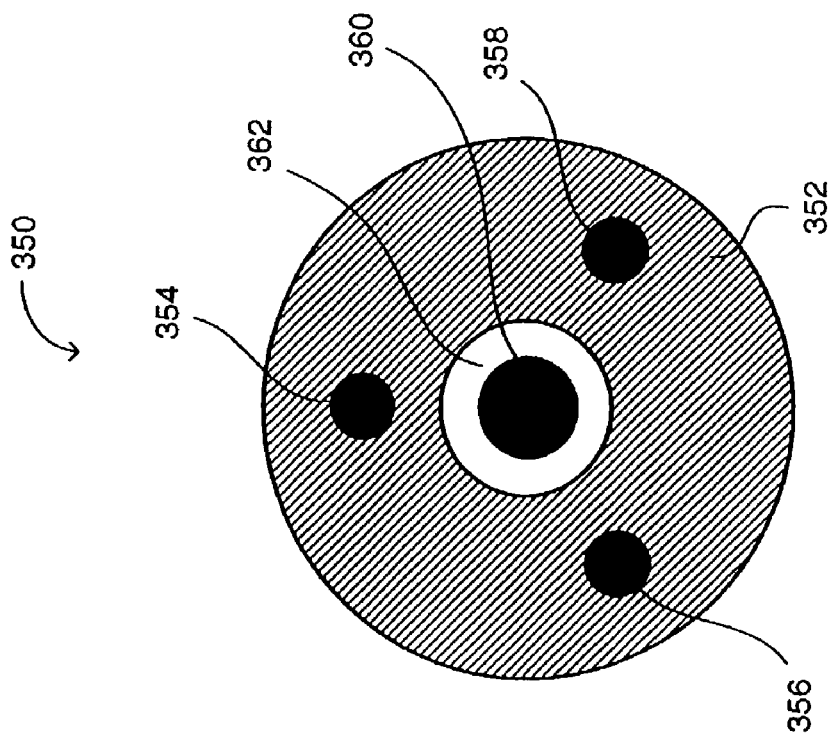
FIG. 8 is a schematic illustration of a lateral cross section of the distal end of the medical catheter of a system for determining position and orientation, such as shown in FIG. 1A, constructed and operative in accordance with another embodiment of the disclosed technique.

Reference is now made to FIG. 8, which is a schematic illustration of a lateral cross section of the distal end of the medical catheter of a system for determining position and orientation, such as shown in FIG. 1A, generally referenced 350, constructed and operative in accordance with another embodiment of the disclosed technique. Medical catheter 350 includes an elongated member 352, electrical conductors 354 and 356 and a support element 358. A guidewire 360 passes through a guidewire lumen 362 within elongated member 352.

Each of electrical conductors 354 and 356 is similar to electrical conductors 306 and 308, as described herein above in connection with FIG. 7A. Support element 358 can be made of a material whose physical properties are substantially similar to those of either one of electrical conductors 354 or 356, but support element 358 can be made of other materials or have other properties. Electrical conductors 354 and 356 and support element 358 are located equally apart on a circle (not shown), which is substantially concentric with the longitudinal axis of elongated member 352 (i.e., on radial lines whose angle there between is approximately 120 degrees).

In this manner, electrical conductors 354 and 356 and support element 358, modify the mechanical properties of elongated member 352, as described herein above in connection with wiring 136 (FIG. 1C). Analogously, any number of electrical conductors and support elements can be distributed in the lateral cross section of the elongated member, according to the desired mechanical properties of the elongated member.

Figure 9:
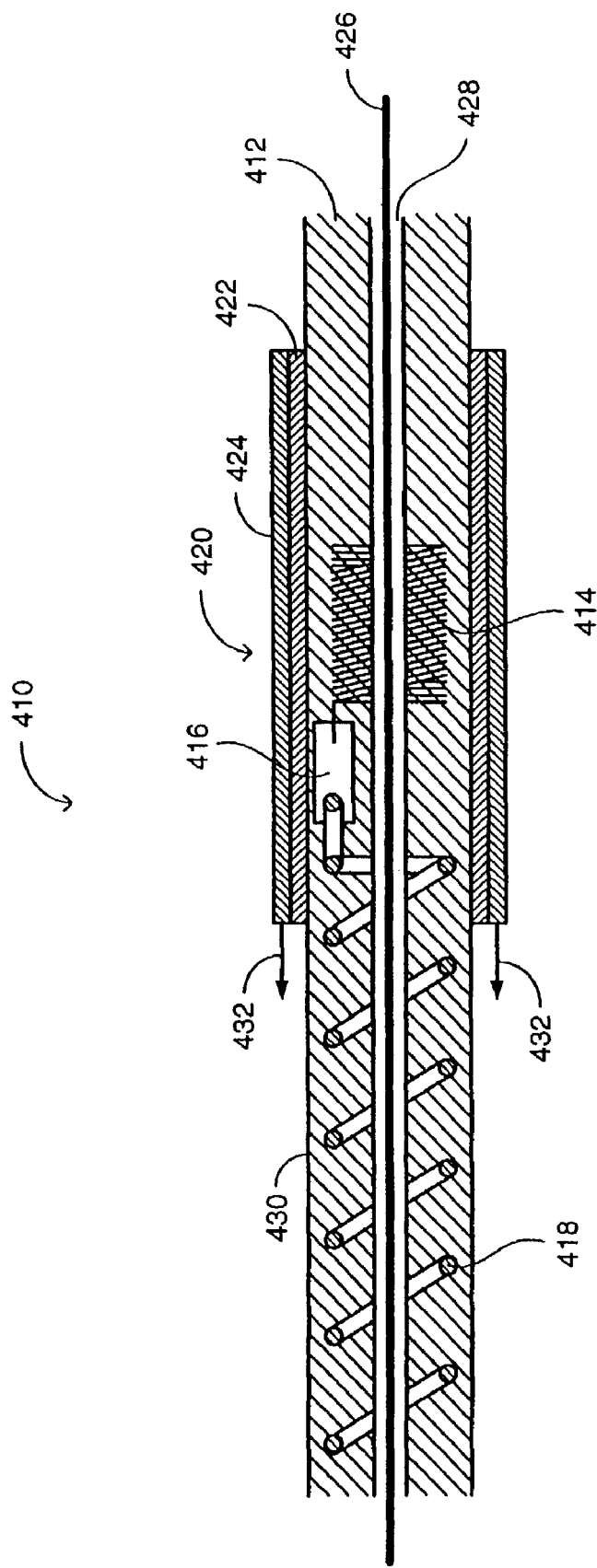
FIG. 9 is a schematic illustration of a longitudinal cross section of the distal end of the medical catheter of a system for determining position and orientation, such as shown in FIG. 1A, constructed and operative in accordance with a further embodiment of the disclosed technique.

Reference is now made to FIG. 9, which is a schematic illustration of a longitudinal cross section of the distal end of the medical catheter of a system for determining position and orientation, such as shown in FIG. 1A, generally referenced 410, constructed and operative in accordance with a further embodiment of the disclosed technique. Medical catheter 410 includes an elongated member 412, an electromagnetic field detector 414, a PCB 416, a wiring 418 and a medical operational element 420. Medical catheter 410 is a stent type catheter Hence, medical operational element 420 includes a stent 422 and a sleeve 424. A guidewire 426 can pass within a guidewire lumen 428, within elongated member 412.

Elongated member 412, electromagnetic field detector 414, PCB 416 and wiring 418 are similar to elongated member 108 (FIG. 1A), electromagnetic field detector 114, PCB 138 and wiring 136, respectively, as described herein above in connection with FIG. 1C. Electromagnetic field detector 414, PCB 416 and wiring 418 are embedded within elongated member 412, in a manner similar to one described herein above in connection with FIG. 1C. Distal ends (not shown) of wiring 418 are coupled with two ends (not shown) of electromagnetic field detector 414, via PCB 416. Proximal ends (not shown) of wiring 418 are coupled with an MPS similar to MPS 106 (FIG. 1A).

Stent 422 is a spring type stent (i.e., self expandable stent) as known in the art, which tends to expand, if no restraint is imposed thereon. During assembly of medical operational element 420 on elongated member 412, stent 422 is passed over an outer wall 430 of elongated member 412 together with restraining sleeve 424, such that sleeve 424 keeps stent 422 in a compressed state. In order to activate medical operational element 420, sleeve 424 is pulled in a direction designated by arrows 432, wherein stent 422 expands and leaves outer wall 430.

Alternatively, stent 422 is made of a shape memory alloy (SMA), such as nickel-titanium (nitinol), and the like, and sleeve 424 is disposed of. The SMA stent is constructed such that when the metallurgical structure of the SMA stent changes from a first phase (e.g., Martensite) to a second phase (e.g., Austenite), the SMA stent expands.

Figure 10:
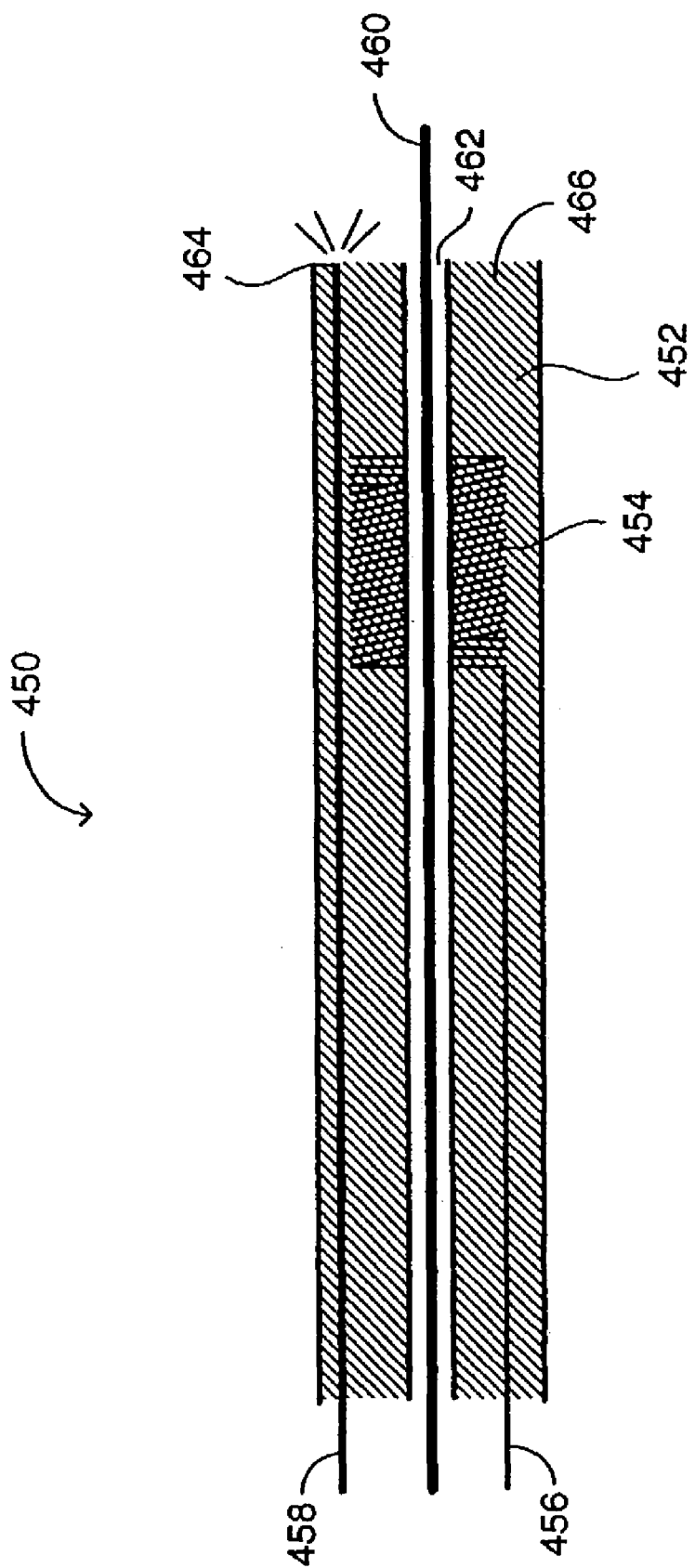
FIG. 10 is a schematic illustration of a longitudinal cross section of the distal end of the medical catheter of a system for determining position and orientation, such as shown in FIG. 1A, constructed and operative in accordance with another embodiment of the disclosed technique.

Reference is now made to FIG. 10, which is a schematic illustration of a longitudinal cross section of the distal end of the medical catheter of a system for determining position and orientation, such as shown in FIG. 1A, generally referenced 450, constructed and operative in accordance with another embodiment of the disclosed technique. Medical catheter 450 includes an elongated member 452, an electromagnetic field detector 454, a wiring 456 and an optical fiber 458. Elongated member 452 and electromagnetic field detector 454 are similar to elongated member 108 (FIG. 1A) and electromagnetic field detector 114 (FIG. 1C), respectively, as described herein above. Wiring 456 is similar to either wiring 136 (FIG. 1C) or wiring 142 (FIG. 1D), as described herein above. Electromagnetic field detector 454 and wiring 456 are embedded within elongated member 452, in a manner similar to the one described herein above in connection with FIG. 1C. A guidewire 460 can pass through a guidewire lumen 462, within elongated member 452.

Optical fiber 458 is embedded within elongated member 452. A distal end 464 of optical fiber 458 is located at a distal end 466 of elongated member 452. Distal end 464 can point either toward the front of distal end 466, or toward a side (not shown) of distal end 466. A proximal end (not shown) of optical fiber 458 is coupled to a laser (not shown). When the laser is activated, optical fiber 458 ablates a tissue (not shown), which is located in the vicinity of distal end 466.

Figure 11:
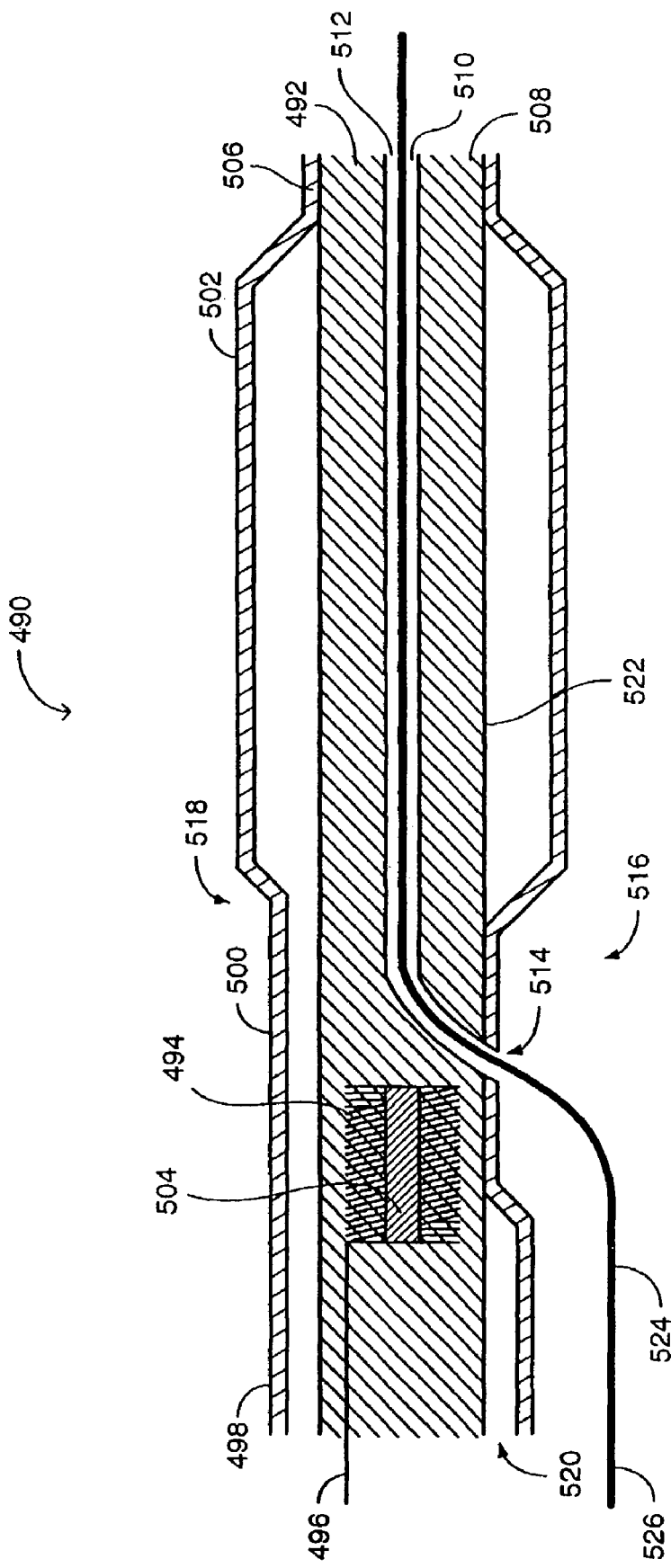
FIG. 11 is a schematic illustration of a longitudinal cross section of the distal end of a medical catheter of the rapid-exchange type, constructed and operative in accordance with a further embodiment of the disclosed technique.

Reference is now made to FIG. 11, which is a schematic illustration of a longitudinal cross section of the distal end of a medical catheter of the rapid-exchange type, generally referenced 490, constructed and operative in accordance with a further embodiment of the disclosed technique. Rapid-exchange catheter is also known in the art as Single Operator Exchange (SOE). Medical catheter 490 includes an elongated member 492, an electromagnetic field detector 494, a wiring 496 and a medical operational element 498. Medical catheter 490 is a balloon type catheter. Therefore, medical operational element 498 includes a tube portion 500 and a balloon portion 502.

Wiring 496 is similar to either wiring 136 (FIG. 1C) or wiring 142 (FIG. 1D), as described herein above. Electromagnetic field detector 494 is made of an electrical conductor (not shown), wound around a core 504. Core 504 is made of a material whose permeability is substantially greater than that of the air. Hence, core 504 can be made of a ferromagnetic material (e.g., ferrite, iron, Mu-metal, superalloy, soft ferrite), and the like, as well as a paramagnetic material. Electromagnetic field detector 494 is embedded within elongated member 492. Wiring 496 is embedded within elongated member 492 in a manner similar to the one described herein above in connection with FIG. 1C. Distal ends (not shown) of wiring 496 are coupled with two ends (not shown) of electromagnetic field detector 494. Proximal ends (not shown) of wiring 496 are coupled with an MPS, similar to MPS 106 (FIG. 1A). A distal end 506 of balloon portion 502 is coupled with a distal end 508 of elongated member 492, in a manner similar to the one described herein above, in connection with FIG. 1C.

Elongated member 492 includes a guidewire lumen 510, whose entrance 512 is located at distal end 508 and whose exit 514 is located at a side portion 516 of elongated member 492. Side portion 516 is located at a proximal end 518 of balloon portion 502. Electromagnetic field detector 494 is located proximal to exit 514 (i.e., adjacent to proximal end 518). A concentric fluid lumen 520 formed between tube portion 500 and an outer wall 522 of elongated member 492, is coupled with a pressurized fluid source similar to the one described herein above, in connection with FIG. 1A.

A region of tube portion 500 in the vicinity of side portion 516 is coupled with side portion 516, in order to prevent fluid communication between guidewire lumen 510 and concentric fluid lumen 520. Tube portion 500 is perforated at side portion 516, in order to keep exit 514 open. In order to guide medical catheter 490 over a guidewire 524, the physician enters a proximal end 526 of guidewire 524 through entrance 512, until proximal end 526 of guidewire 524 passes through guidewire lumen 510 and exits guidewire lumen 510 at exit 514. This mode of operation is known in the art as "rapid-exchange".

It is noted that since a portion of elongated member 492 proximal to exit 514 is solid, it is possible to incorporate core 504 with electromagnetic field detector 494. Furthermore, since core 504 is made of a ferromagnetic material, electromagnetic field detector 494 is more sensitive to the electromagnetic field generated by a transmitter similar to transmitter 134 (FIG. 1A), than an electromagnetic field detector similar to electromagnetic field detector 114 (FIG. 1C).

Figure 12:
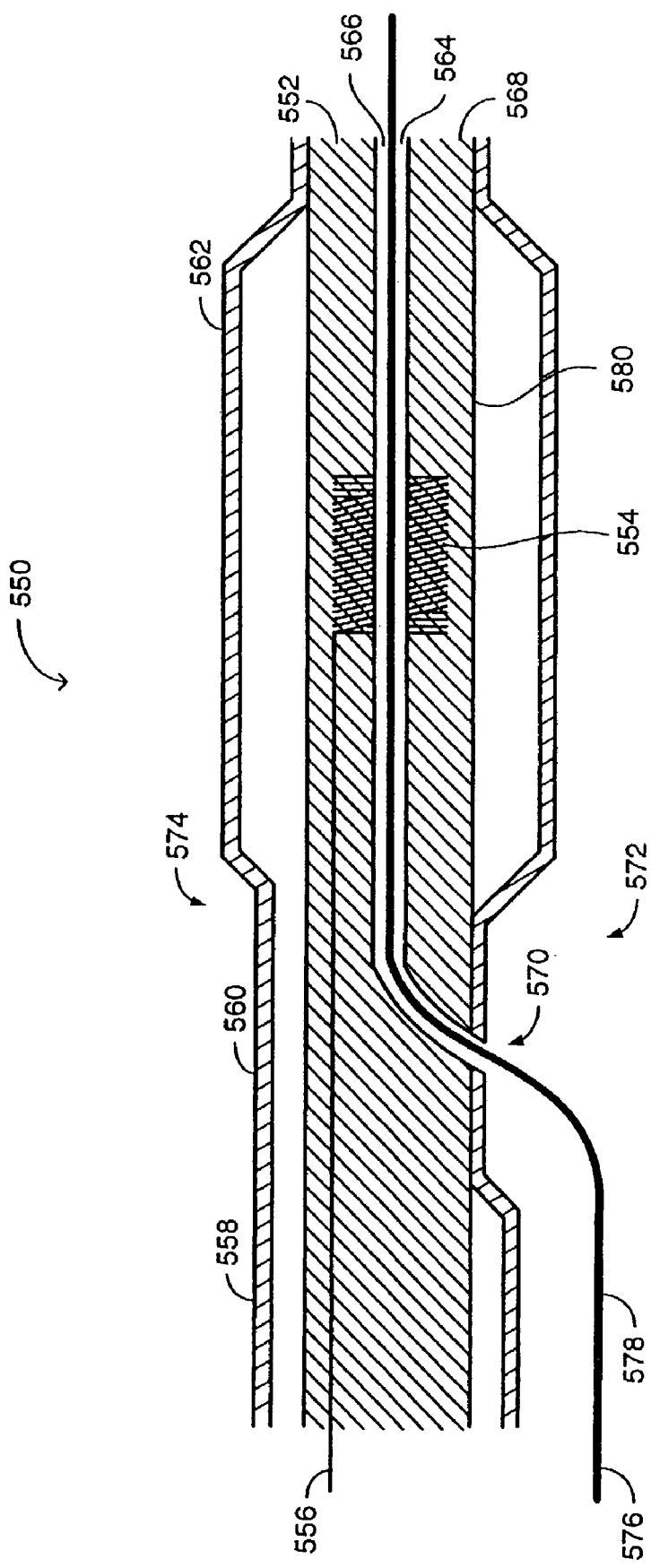
FIG. 12 is a schematic illustration of a longitudinal cross section of the distal end of a medical catheter of the rapid-exchange type, constructed and operative in accordance with another embodiment of the disclosed technique.

Reference is now made to FIG. 12, which is a schematic illustration of a longitudinal cross section of the distal end of a medical catheter of the rapid-exchange type, generally referenced 550, constructed and operative in accordance with another embodiment of the disclosed technique. Medical catheter 550 includes an elongated member 552, an electromagnetic field detector 554, a wiring 556 and a medical operational element 558. Medical catheter 550 is a balloon type catheter. Therefore, medical operational element 558 includes a tube portion 560 and a balloon portion 562. Medical operational element 558 is similar to medical operational element 498 (FIG. 11), as described herein above. Medical operational element 558 is constructed in a manner similar to the one described herein above in connection with FIG. 11.

Elongated member 552 includes a guidewire lumen 564, whose entrance 566 is located at a distal end 568 of elongated member 552. An exit 570 of guidewire lumen 564 is located at a side portion 572 of elongated member 552. Side portion 572 is located at a proximal end 574 of balloon portion 562.

Guidewire lumen 564 is similar to guidewire lumen 510 (FIG. 11), as described herein above. Electromagnetic field detector 554 is similar to electromagnetic field detector 114 (FIG. 1C), as described herein above. Wiring 556 is similar to either wiring 136 (FIG. 1C) or wiring 142 (FIG. 1D), as described herein above. Distal ends (not shown) of wiring 556 are coupled with two ends (not shown) of electromagnetic field detector 554. Proximal ends (not shown) of wiring 556 are coupled with an MPS, similar to MPS 106 (FIG. 1A).

Electromagnetic field detector 554 is embedded within elongated member 552 as described herein above in connection with FIG. 1C, such that guidewire lumen 564 passes through the winding of electromagnetic field detector 554. Electromagnetic field detector 554 is embedded in such a location within elongated member 552, that when balloon portion 562 expands, balloon portion 562 encompasses electromagnetic field detector 554.

The physician enters a proximal end 576 of a guidewire 578 into guidewire lumen 564 through entrance 566, passes guidewire 578 through guidewire lumen 564 and pushes guidewire lumen 564 out through exit 570. Medical catheter 550 operates in rapid-exchange mode, while electromagnetic field detector 554 is located such that balloon portion 562 encompasses electromagnetic field detector 554, when balloon portion 562 expands. Thus, medical catheter 550 allows the MPS to determine the location of medical operational element 558, more accurately than that of medical catheter 490 (FIG. 11).

Alternatively, the electromagnetic field detector is wound around an outer wall 580 of elongated member 552. Further alternatively, the electromagnetic field detector is located proximal to exit 570, while the electromagnetic field detector is either embedded within the elongated member or is wound around the outer wall of the elongated member.

Figure 13:
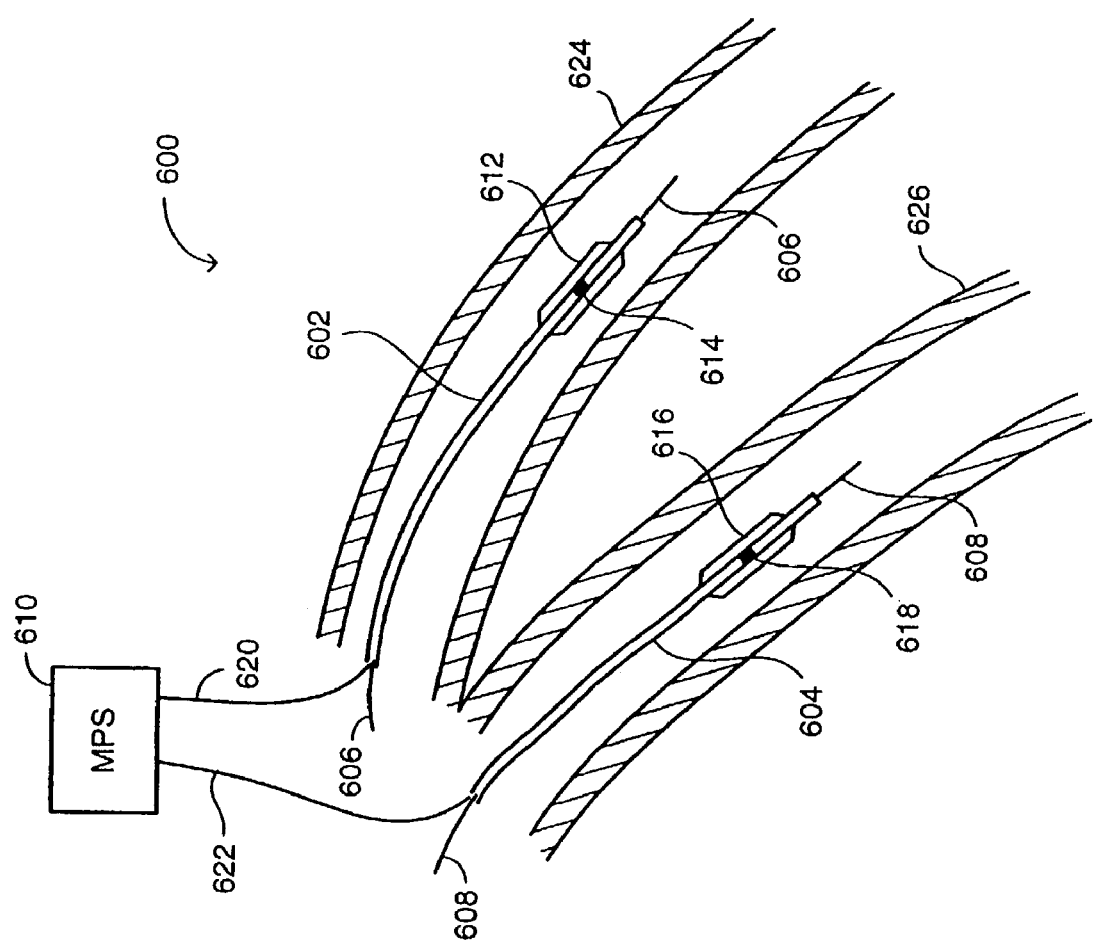
FIG. 13 is a schematic illustration of a system for determining the relative positions and orientations of a plurality of medical catheters, constructed and operative in accordance with a further embodiment of the disclosed technique.

Reference is now made to FIG. 13, which is a schematic illustration of a system for determining the relative positions and orientations of a plurality of medical catheters, generally referenced 600, constructed and operative in accordance with a further embodiment of the disclosed technique. System 600 includes a plurality of medical catheters 602 and 604, a plurality of guidewires 606 and 608 and an MPS 610. Each of medical catheters 602 and 604 is similar to either medical catheter 102 (FIG. 1A), medical catheter 490 (FIG. 11) or medical catheter 550 (FIG. 12), as described herein above. MPS 610 is similar to MPS 106 (FIG. 1A), as described herein above.

Medical catheter 602 includes a medical operational element 612 and an electromagnetic field detector 614. Medical catheter 604 includes a medical operational element 616 and an electromagnetic field detector 618. Each of medical operational elements 612 and 616 is similar to medical operational element 112 (FIG. 1A), as described herein above. If a guidewire lumen (not shown) within an elongated member (not shown) of each of medical catheter 602 and 604, is similar to guidewire lumen 116 (FIG. 1C), then each of electromagnetic field detectors 614 and 618 is similar to electromagnetic field detector 114 (FIG. 1C) or electromagnetic field detector 186 (FIG. 3), as described herein above. If the guidewire lumen within the elongated member of each of medical catheter 602 and 604, is similar to guidewire lumen 510 (FIG. 11), then each of electromagnetic field detectors 614 and 618 is similar to electromagnetic field detector 494, as described herein above.

Electromagnetic field detectors 614 and 618 are coupled to MPS 610, via wirings 620 and 622, respectively. Each of wirings 620 and 622 is similar to wiring 136 (FIG. 1C), as described herein above. Medical catheters 602 and 604 are passed over guidewires 606 and 608, respectively, into lumens 624 and 626, respectively, of a patient (not shown). Electromagnetic field detectors 614 and 618 detect the electromagnetic field generated by a transmitter (not shown) of MPS 610 and provide MPS 610 respective signals, via wirings 620 and 622, respectively. MPS 610 determines the position and orientation of medical operational element 612 relative to medical operational element 616, according to the signals received from electromagnetic field detectors 614 and 618.

Figure 14:
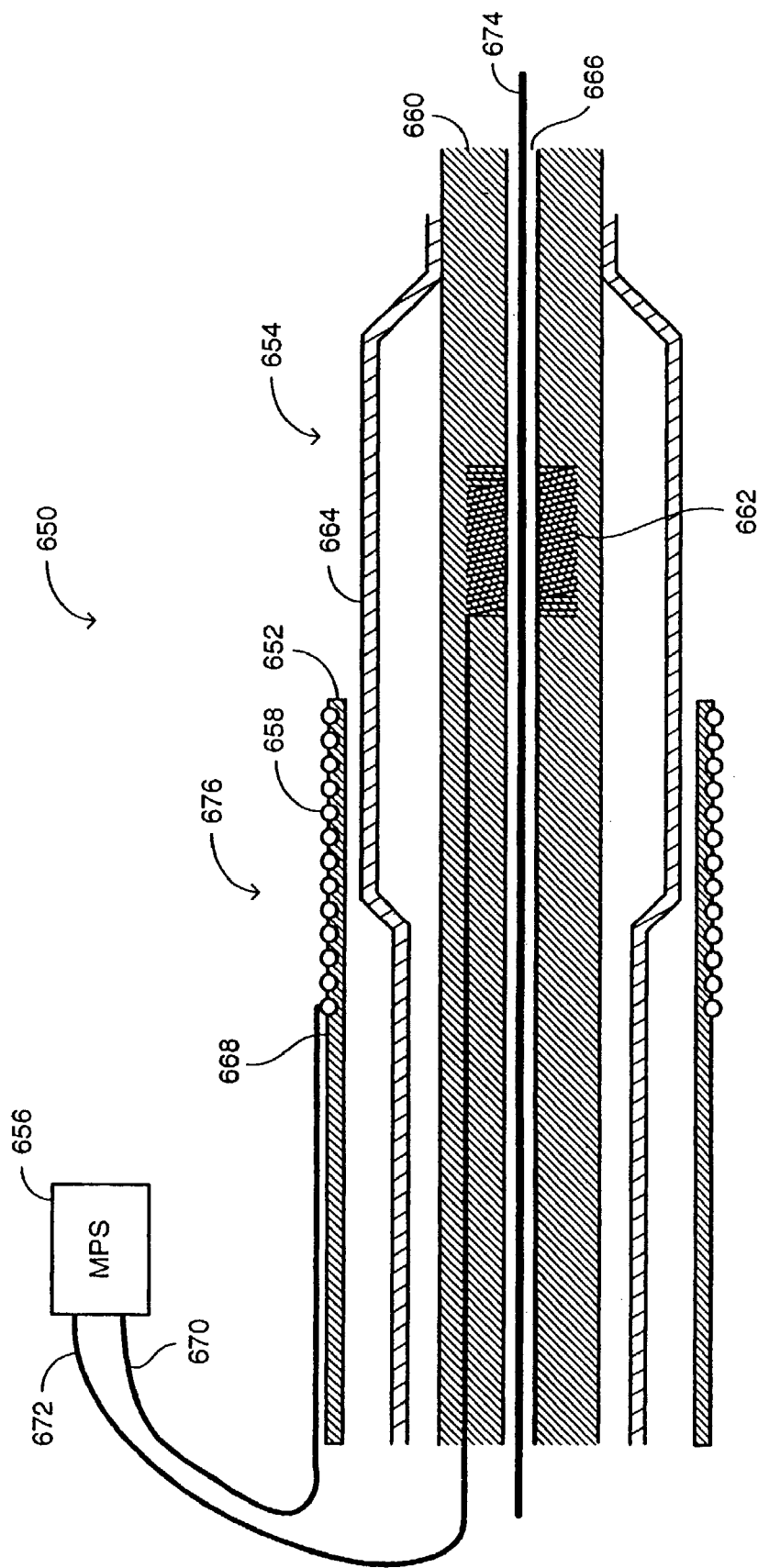
FIG. 14 is a schematic illustration of a system for determining the position and orientation of a guiding catheter, constructed and operative in accordance with another embodiment of the disclosed technique.

Reference is now made to FIG. 14, which is a schematic illustration of a system for determining the position and orientation of a guiding catheter, generally referenced 650, constructed and operative in accordance with another embodiment of the disclosed technique. System 650 includes a guiding catheter 652, a medical catheter 654 and an MPS 656. Guiding catheter 652 includes an electromagnetic field detector 658. Medical catheter 654 includes an elongated member 660, an electromagnetic field detector 662 and a medical operational element 664. Elongated member 660 includes a guidewire lumen 666.

Guidewire lumen 666 is either similar to guidewire lumen 116 (FIG. 1C) or guidewire lumen 510 (FIG. 11), as described herein above. Electromagnetic field detector 662 is similar to either electromagnetic field detector 114 (FIG. 1C), electromagnetic field detector 186 (FIG. 3), or electromagnetic field detector 494 (FIG. 11), according to the type of guidewire lumen 666. Medical operational element 664 is similar to medical operational element 112 (FIG. 1C), as described herein above. Electromagnetic field detector 662 is located at an activation site (not shown) of medical operational element 664.

Electromagnetic field detector 658 is made of an electric conductor wound around an outer wall 668 of guiding catheter 652. Alternatively, the electromagnetic field detector is located within a wall of the guiding catheter. Electromagnetic field detector 658 is coupled with MPS 656 via a wiring 670. Wiring 670 is wound around outer wall 668. Alternatively, wiring 670 lies in a substantially straight line on outer wall 668. Electromagnetic field detector 658 and wiring 670 are coated with a protective layer, such as an adhesive, and the like. The protective layer provides mechanical and electrical protection to electromagnetic field detector 658 and to wiring 670. The protective layer is coated with a lubricant to facilitate the travel of guiding catheter 652 within a lumen (not shown) of a patient (not shown).

Electromagnetic field detector 662 is coupled with MPS 656, via a wiring 672. Wiring 672 is similar to either wiring 136 (FIG. 1C) or wiring 142 (FIG. 1D), as described herein above. Medical catheter 654 is located within guiding catheter 652. A guidewire 674 passes through guidewire lumen 666.

Electromagnetic field detector 658 detects an electromagnetic field generated by a transmitter (not shown) of MPS 656 and provides a respective signal to MPS 656, via wiring 670. Electromagnetic field detector 662 detects an electromagnetic field generated by the transmitter and provides a respective signal to MPS 656, via wiring 672. MPS 656 determines the position and orientation of electromagnetic field detector 658 in a reference coordinate system, according to the signal received from electromagnetic field detector 658. If electromagnetic field detector 658 is located at a distal end 676 of guiding catheter 652, then MPS 656 determines the position and orientation of distal end 676 in the reference coordinate system. Alternatively, MPS 656 determines the position and orientation of electromagnetic field detector 662 (i.e., the activation site of medical operational element 664), relative to electromagnetic field detector 658 (i.e., distal end 676), according to signals received from electromagnetic field detectors 658 and 662.

Figure 15:
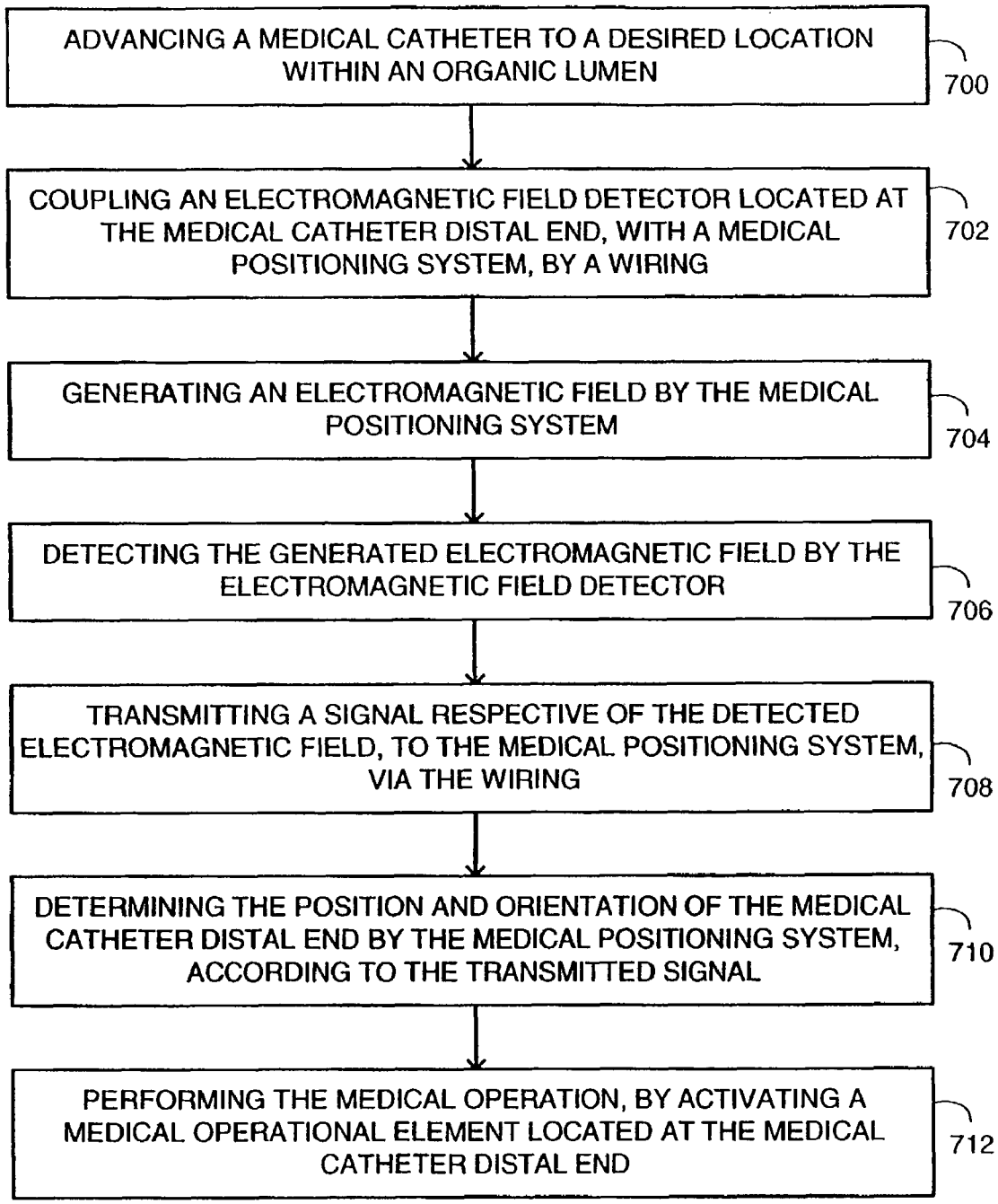
FIG. 15 is a schematic illustration of a method for operating the system of FIG. 1A, operative in accordance with a further embodiment of the disclosed technique.

Reference is now made to FIG. 15, which is a schematic illustration of a method for operating the system of FIG. 1A, operative in accordance with a further embodiment of the disclosed technique. In procedure 700, a medical catheter is advanced to the desired location within an organic lumen.

Prior to procedure 700, a guiding catheter can be advanced to an approximate location proximal to a desired location within an organic lumen. Additionally, the guidewire can be advanced within the guiding catheter to the desired location, past a guiding catheter distal end. With reference to FIG. 1A, in case a guidewire was previously inserted through the guiding catheter, the physician inserts the proximal end of guidewire 104 into distal end 144 of medical catheter 102 and advances medical catheter 102 to the desired location within a lumen of a patient, over guidewire 104. At this stage, the physician can view an image of guidewire 104 on an imaging device, such as radiographic, fluoroscopic, magnetic, sonographic device, and the like. In case no guidewire was previously employed, the physician advances the medical catheter to the desired location, through the guiding catheter. Optionally, with reference to FIG. 14, electromagnetic field detector 658 is mounted at distal end 676 of guiding catheter 652, thereby allowing detection of the position and orientation of guiding catheter 652 without employing X-ray or fluoroscopy, and with the precision of MPS.

In procedure 702, an electromagnetic field detector located at a medical catheter distal end, is coupled with an MPS by a wiring. According to a preferable embodiment, the wiring affects the mechanical properties of the medical catheter, such as the pushability and trackability of the medical catheter through the organic lumen (when the medical catheter extends beyond the guiding catheter distal end). With reference to FIGS. 1A and 1C, electromagnetic field detector 114 which is located at distal end 114 of medical catheter 102, is coupled with MPS 106, via wiring 136. Since wiring 136 is spirally embedded within elongated member 108, the mechanical properties of elongated member 108, such as pushability and trackability of elongated member 108 through the lumen, are modified. It is noted that wiring 136 can be embedded within elongated member 108 in a substantially straight line, or a combination of spiral and straight sections, wherein wiring 136 still modifies the mechanical properties of elongated member 108.

In procedure 704, an electromagnetic field is generated by the MPS. With reference to FIG. 1A, transmitter 134 generates an electromagnetic field. In procedure 706, the generated electromagnetic field is detected by the electromagnetic field detector.

In procedure 708, a signal respective of the detected electromagnetic field is transmitted to the MPS, via the wiring. With reference to FIG. 1A, electromagnetic field detector 114 detects the electromagnetic field generated by transmitter 134 and electromagnetic field detector 114 transmits a signal respective of the detected electromagnetic field, to detector interface 124, via wiring 136.

In procedure 710, the position and orientation of the medical catheter distal end is determined by the MPS, according to the transmitted signal. With reference to FIG. 1A, processor 126 receives from detector interface 124, the signal which was transmitted to detector interface 124 by electromagnetic field detector 114 and processor 126 determines the position and orientation of distal end 144 of medical catheter 102, according to the transmitted signal.

In procedure 712, a medical operation is performed by activating a medical operational element located at the medical catheter distal end. With reference to FIGS. 1A and 1B, the physician inflates balloon portion 120 by introducing a fluid from a pressurized fluid source, into tube portion 118.

It will be appreciated by persons skilled in the art that the disclosed technique is not limited to what has been particularly shown and described hereinabove. Rather the scope of the disclosed technique is defined only by the claims, which follow.

The invention claimed is:

1. Catheter for performing a medical operation on an organic lumen, the catheter comprising:
   an elongated member comprising substantially flexible material;
   a medical operational element located at a distal end of said elongated member;
   an electromagnetic field detector located at said distal end, said electromagnetic field detector operative to detect an electromagnetic field generated by a medical positioning system that is proximal of said elongated member distal end; and
   a wiring for coupling said electromagnetic field detector with said medical positioning system, said wiring operative to transmit a signal respective of said detected electromagnetic field to said medical positioning system, said wiring being separate and isolated from said medical operational element and from said electromagnetic field detector, said wiring embedded within substantially the entirety of said elongated member between said medical positioning system and said electromagnetic field detector such that said wiring is positioned within the wall of said elongated member and is surrounded, in said embedded portion, by said substantially flexible material of said elongated member,
   wherein said medical positioning system determines the position and orientation of said distal end, relative to a reference coordinate system, according to said transmitted signal, and
   wherein said elongated member has a mechanical property of one of rigidity, elasticity, and plasticity, and wherein said mechanical property of the part of said elongated member between said medical positioning system and said electromagnetic field detector where said wiring is embedded is increased or decreased due to said mechanical property of said wiring, irrespective of any modified mechanical property resulting from said medical operational element or from said electromagnetic field detector, such that the increase or decrease in said mechanical property of the part of said elongated member between said medical positioning system and said electromagnetic field detector where said wiring is embedded enhances the maneuverability of said catheter within said organic lumen throughout the stages of: insertion of said catheter into the organic lumen, performance of the medical operation with said medical operational element, and removal of said catheter from the organic lumen.

2. Position and orientation determination system comprising:
   a guiding catheter;
   a guiding catheter electromagnetic field detector located at a guiding catheter distal end of said guiding catheter, said guiding catheter electromagnetic field detector being coupled with a medical positioning system; and
   at least one medical catheter located within said guiding catheter, said at least one medical catheter comprising:
      an elongated member comprising substantially flexible material;
      a medical operational element located at least one medical catheter distal end of a respective one of said at least one medical catheter;
      a medical catheter electromagnetic field detector located at said at least one medical catheter distal end, said medical catheter electromagnetic field detector operative to detect an electromagnetic field generated by said medical positioning system that is proximal of said elongated member distal end, and
      a wiring for coupling said medical catheter electromagnetic field detector with said medical positioning system, said wiring operative to transmit a signal respective of said detected electromagnetic field to said medical positioning system, said wiring being separate and isolated from said medical operational element and from said electromagnetic field detector, said wiring embedded within substantially the entirety of said elongated member between said medical positioning system and said electromagnetic field detector such that said wiring is positioned within the wall of said elongated member and is surrounded, in said embedded portion, by said substantially flexible material of said elongated member, said elongated member having a mechanical property of one of rigidity, elasticity, and plasticity, and wherein said mechanical property of the part of said elongated member between said medical positioning system and said electromagnetic field detector where said wiring is embedded is increased or decreased due to said mechanical property of said wiring irrespective of any modified mechanical property resulting from said medical operational element or from said electromagnetic field detector, such that the increase or decrease in said mechanical property of the part of said elongated member between said medical positioning system and said electromagnetic field detector where said wiring is embedded enhances the maneuverability of said catheter within said organic lumen throughout the stages of: insertion of said catheter into the organic lumen, performance of the medical operation with said medical operational element, and removal of said catheter from the organic lumen, wherein said medical positioning system determines the position and orientation of said at least one medical catheter distal end, relative to a reference coordinate system, according to said transmitted signal, and wherein said medical positioning system determines the position and orientation of said guiding catheter distal end.

3. A catheter for performing a medical operation on an organic lumen, comprising:

an elongated member having proximal and distal ends, said elongated member comprising substantially flexible material;

a medical operational element located at said distal end;

an electromagnetic field detector located at said distal end configured to detect an electromagnetic field generated by a medical positioning system and produce a signal respective of said detected field, said medical positioning system being configured to determine a position and orientation of said detector, relative to a reference coordinate system, according to said signal;

a wiring, different from said medical operational element and said field detector, coupled to said detector for transmitting said signal, said wiring being embedded within and along at least a part of said elongated member extending away from said distal end such that said wiring is positioned within the wall of said elongated member and is surrounded, in said embedded portion, by said substantially flexible material of said elongated member said elongated member having a mechanical property, and wherein said mechanical property of said part of said elongated member where said wiring is embedded is increased or decreased due to said wiring;

wherein said wiring along at least said part of said elongated member has a form selected from the group comprising a straight form, a first spiral form having a substantially constant pitch, a second spiral form having a plurality of pitches, and a combination form having one or more of the foregoing.

4. The catheter of claim 3 wherein said elongated member includes a guidewire lumen for a guidewire to pass therethrough.

5. The catheter of claim 4 wherein said electromagnetic field detector is located at a side of said guidewire lumen.

6. The catheter of claim 4 wherein said electromagnetic field detector is in form of a coil which surrounds at least a portion of said guidewire lumen.

7. The catheter of claim 4 wherein said electromagnetic field detector is wound around a core comprising magnetically-permeable material, said electromagnetic field detector being located proximal to said guidewire lumen proximal end.

8. The catheter of claim 3 wherein said mechanical property is selected from the group consisting of:
pushability;
trackability;
rigidity;
elasticity;
plasticity;
flexibility;
modulus of elasticity; and
coefficient of rigidity.

9. The catheter of claim 3 wherein said wiring takes said combination form wherein at least a portion of said wiring is wound in a spiral form having a pitch of at least one value, along the length of said elongated member, and wherein at least another portion of said wiring is substantially straight along the length of said elongated member.

10. The catheter of claim 3 wherein said wiring is coated with an electrically shielding coating.

11. The catheter of claim 3 wherein said wiring comprises one of twisted pair conductors, coaxial conductors and tri-axial conductors.

12. The catheter of claim 3 wherein said wiring comprises first and second conductors, said first electrical conductor being embedded within said elongated member along a first path, said second electrical conductor being embedded within said elongated member along a second path, and wherein said first path and said second path substantially lie on a plane, said plane substantially passing through the longitudinal axis of said elongated member, and wherein said first path and second path are substantially equally spaced from said longitudinal axis.

13. The catheter of claim 3 wherein a first electrical conductor of said wiring, a second electrical conductor of said wiring, and a support element, are all embedded within said elongated member in substantially straight lines, and wherein said first electrical conductor, said second electrical conductor and said support element substantially lie equally apart on a circle, said circle being substantially concentric with it longitudinal axis in a lateral cross section of said elongated member.

14. The catheter of claim 3 further comprising a radiopaque marker embedded within said elongated member at said distal end.

15. The catheter of claim 3 wherein said medical operational element is selected from the group consisting of:
balloon;
stent;
balloon expanding stent;
laser;
cryogenic fluid unit;
electric impulse unit;
cutting balloon;
rotational atherectomy unit;
directional atherectomy unit;
transluminal extraction unit;
coated stent;
drug delivery balloon;
brachytherapy unit;
valve;

suturing device;
implant;
biological marker;
radiopaque marker;
substance delivery device;
imaging device;
diagnostic device;
miniature camera;
infrared camera;
optical coherence tomography;
magnetic resonance imaging;
ultrasound; and
sensor.

16. The catheter of claim 15 wherein said stent comprises a shape memory alloy material.

17. The catheter of claim 3 wherein said catheter further comprises a transmitter, said transmitter being coupled to a proximal end of said wiring; and
wherein said transmitter wirelessly couples said electromagnetic field detector with said medical positioning system.

18. The catheter of claim 3 further comprising a shielding covering at least a portion of said electromagnetic field detector, wherein said shielding is of such physical dimensions and properties, that said shielding shields said electromagnetic field detector against at least one electromagnetic field source.

19. A system for determining position and orientation, comprising:
a guiding catheter;
a guiding catheter electromagnetic field detector located at a guiding catheter distal end of said guiding catheter, said guiding catheter electromagnetic field detector being coupled with a medical positioning system; and
at least one medical catheter located within said guiding catheter, said at least one medical catheter comprising:
an elongated member having medical catheter proximal and distal ends, said elongated member comprising substantially flexible material;
a medical operational element located at said medical catheter distal end;
an medical catheter electromagnetic field detector located at said medical catheter distal end configured to detect an electromagnetic field generated by said medical positioning system and produce a signal respective of said detected field, said medical positioning system being configured to determine a position and orientation of said medical catheter field detector, relative to a reference coordinate system, according to said signal;
a wiring, different from said medical operational element and said medical catheter field detector, coupled to said medical catheter field detector for transmitting said signal, said wiring being embedded within and along at least a part of said elongated member extending away from said medical catheter distal end such that said wiring is positioned within the wall of said elongated member and is surrounded, in said embedded portion, by said substantially flexible material of said elongated member, said elongated member having a mechanical property, and wherein said mechanical property of said part of said elongated member where said wiring is embedded is increased or decreased due to said wiring;
wherein said wiring along at least said part of said elongated member takes a form selected from the group comprising a straight form, a first spiral form having a substantially constant pitch, a second spiral form having a plurality of pitches and a combination form having one or more of the foregoing.

20. The system of claim 19 wherein said guiding catheter electromagnetic field detector is located within a wall of said guiding catheter.

21. The system of claim 19 wherein said elongated member includes a guidewire lumen for a guidewire to pass therethrough.

* * * * *